(12) United States Patent
Devita et al.

(10) Patent No.: US 6,211,174 B1
(45) Date of Patent: Apr. 3, 2001

(54) NAPHTHO-FUSED LACTAMS PROMOTE RELEASE OF GROWTH HORMONE

(75) Inventors: Robert J. Devita, Westfield; Matthew J. Wyvratt, Mountainside, both of NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/159,451

(22) Filed: Sep. 24, 1998

Related U.S. Application Data

(60) Provisional application No. 60/063,948, filed on Oct. 31, 1997.

(51) Int. Cl.[7] .................... C07D 223/14; C07D 223/16; A61K 31/55
(52) U.S. Cl. .................................... 514/217; 540/522
(58) Field of Search .............................. 514/217; 540/522

(56) References Cited

U.S. PATENT DOCUMENTS

| | | | |
|---|---|---|---|
| 5,206,235 | 4/1993 | Fisher et al. | 514/213 |
| 5,283,241 | 2/1994 | Bochis et al. | 514/183 |
| 5,284,841 | 2/1994 | Chu et al. | 514/183 |
| 5,310,737 | 5/1994 | Fisher | 514/215 |
| 5,317,017 | 5/1994 | Ok et al. | 514/211 |
| 5,374,721 | 12/1994 | Schoen et al. | 540/491 |
| 5,430,144 | 7/1995 | Schoen et al. | 540/461 |
| 5,434,261 | 7/1995 | Schoen et al. | 540/461 |
| 5,438,136 | 8/1995 | Devita et al. | 540/456 |
| 5,817,654 | * 10/1998 | Thogersen et al. | 514/217 |

FOREIGN PATENT DOCUMENTS

WO 96/05195   2/1996   (WO).

\* cited by examiner

*Primary Examiner*—Bruck Kifle
(74) *Attorney, Agent, or Firm*—J. Eric Thies; David L. Rose

(57) ABSTRACT

The present invention is directed to certain naphtho-fused lactams of the general structural formula:

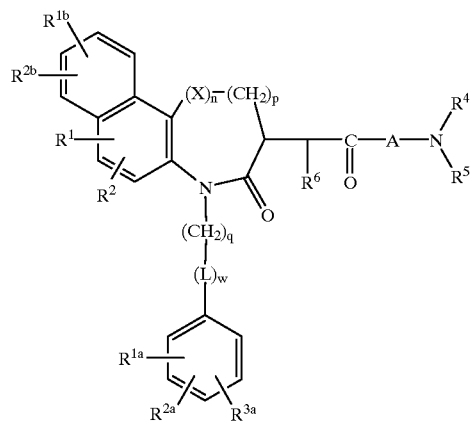

wherein and $R^1$, $R^{1a}$, $R^{1b}$, $R^{2a}$, $R^{2b}$, $R^{3a}$, $R^4$, $R^5$, $R^6$, A, L, X, n, p and w are as defined herein. These compounds promote the release of growth hormone in humans and animals. This property can be utilized to promote the growth of food animals to render the production of edible meat products more efficient, and in humans, to treat physiological or medical conditions characterized by a deficiency in growth hormone secretion, such as short stature in growth hormone deficient children, and to treat medical conditions which are improved by the anabolic effects of growth hormone.

10 Claims, No Drawings

NAPHTHO-FUSED LACTAMS PROMOTE RELEASE OF GROWTH HORMONE

This application claims the benefit of provisional application U.S. application Ser. No. 60/063,948, filed Oct. 31, 1997.

BACKGROUND OF THE INVENTION

Growth hormone, which is secreted from the pituitary, stimulates growth of all tissues of the body that are capable of growing. In addition, growth hormone is known to have the following basic effects on the metabolic processes of the body: (1) Increased rate of protein synthesis in all cells of the body; (2) Decreased rate of carbohydrate utilization in cells of the body; (3) Increased mobilization of free fatty acids and use of fatty acids for energy. A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering GRF or a peptidal compound which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recombinant growth hormone has become available which, while no longer carrying any risk of disease transmission, is still a very expensive product which must be given by injection or by a nasal spray. Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. Non peptidal growth hormone secretagogues are disclosed in e.g., U.S. Pat. Nos. 5,206,235, 5,283,241, 5,284,841, 5,310,737, 5,317,017, 5,374,721, 5,430,144, 5,434,261, 5,438,136, 5,492,916, 5,494,919, 5,494,920, and 5,536,716. Other growth hormone secretagogues are disclosed e.g., in PCT Patent Publications WO 94/13696, WO 94/19367, WO 95/03289, WO 95/03290, WO 95/09633, WO 95/11029, WO 95/12598, WO 95/13069, WO 95/14666, WO 95/16675, WO 95/16692, WO 95/17422, WO 95/17423, WO 95/34311, WO 96/02530, WO 96/05195 and WO 96/22997. The instant compounds are low molecular weight peptide analogs for promoting the release of growth hormone which have good stability in a variety of physiological environments and which may be administered parenterally, nasally or by the oral route.

SUMMARY OF THE INVENTION

The instant invention is directed to certain naphtho-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the naphtho-fused lactam compounds. It is a further object of this invention to describe procedures for the preparation of such compounds. A still further object is to describe the use of such compounds to increase the secretion of growth hormone in humans and animals. A still further object of this invention is to describe compositions containing the naphtho-fused lactam compounds for the use of treating humans and animals so as to increase the level of growth hormone secretions. Further objects will become apparent from a reading of the following description.

DESCRIPTION OF THE INVENTION

The novel naphtho-fused lactams of the instant invention are described by structural Formula I:

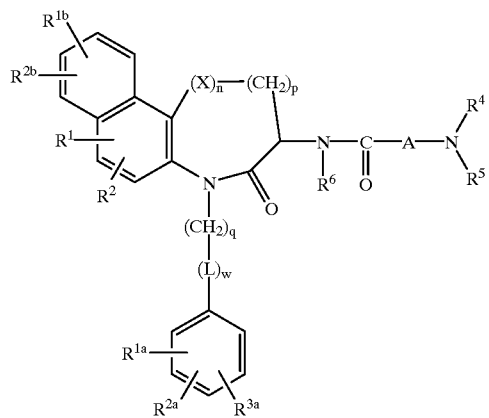

Formula I wherein:

L is:

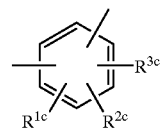

n is 0 or 1;
p is 0 to 3;
q is 0 to 4;
w is 0 or 1;
X is

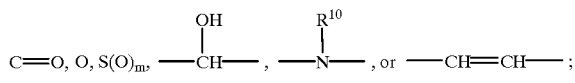

m is 0 to 2;
$R^1$, $R^2$, $R^{1a}$, $R^{2a}$, $R^{1b}$, $R^{2b}$, $R^{1c}$ and $R^{2c}$ are independently selected from the group consisting of: hydrogen, halogen, $C_1$–$C_7$ alkyl, $C_1$–$C_3$ perfluoroalkyl, $C_1$–$C_3$ perfluoroalkoxy, —S(O)$_m$R$^{7a}$, cyano, nitro, R$^{7b}$O(CH$_2$)$_v$—, R$^{7b}$COO(CH$_2$)$_v$—, R$^{7b}$OCO(CH$_2$)$_v$-, R$^4$R$^5$N(CH$_2$)$_v$—, R$^{7b}$CON(R$^4$)(CH$_2$)$_v$—, R$^4$R$^5$NCO (CH$_2$)$_v$—, phenyl, substituted phenyl where the substituents on phenyl are 1 to 3 of halogen, $C_1$–$C_6$ alkyl, $C_1$–$C_6$ alkoxy, or hydroxy;

R$^{7a}$ and R$^{7b}$ are independently selected from the group consisting of: hydrogen, $C_1$–$C_3$ perfluoroalkyl, $C_1$–$C_6$ alkyl, $C_1$–$C_6$ alkyl substituted with phenyl, phenyl and substituted phenyl where the substituents on phenyl are 1 to 3 of halogen, $C_1$–$C_6$ alkyl, $C_1$–$C_6$ alkoxy, or hydroxy;

v is 0 to 3;

R$^{3a}$, R$^{3b}$ and R$^{3c}$ are independently selected from the group consisting of: hydrogen, R$^9$, $C_1$–$C_6$ alkyl substituted with R$^9$, phenyl substituted with R$^9$, or phenoxy substituted with R$^9$ with the proviso that either R$^{3a}$, R$^{3b}$ or R$^{3c}$ must be a substituent other than hydrogen;

R$^9$ is selected from the group consisting of: R$^{4b}$R$^{12b}$NCON (R$^{12a}$)(CH$_2$)$_v$—, R$^{4b}$R$^{12b}$NCSN(R$^{12a}$)(CH$_2$)$_v$—, R$^{4b}$R$^{12c}$NN(R$^{12b}$)CSN(R$^{12a}$)(CH$_2$)$_v$—, R$^{4b}$R$^{12c}$NN(R$^{12b}$)CON(R$^{12a}$)(CH$_2$)$_v$—, R$^{4b}$R$^{12c}$NN(R$^{12b}$)COO(CH$_2$)$_v$—, R$^{4b}$R$^{12b}$NCOO(CH$_2$)$_v$— and R$^{13}$OCON(R$^{12a}$)(CH$_2$)$_v$—;

R$^{10}$ is selected from the group consisting of: hydrogen, $C_1$–$C_6$ alkyl, phenyl $C_1$–$C_6$ alyl and $C_1$–$C_5$ alkanoyl-$C_1$–$C_6$ alkyl; R$_{12a}$, R$^{12b}$ and R$^{12c}$ are independently selected from the group consisting of: R$^{5a}$, OR$^{5a}$, and COR$^{5a}$; or R$^{12a}$ and R$^{12b}$, or R$^{12b}$ and R$^{12c}$, or R$^{12a}$ and R$^{12c}$, or R$^{12b}$ and R$^{4b}$, or R$^{12c}$ and R$^{4b}$, or R$^{13}$ and R$^{12a}$ can be taken together to form the group —CH$_2$)$_r$—B—(CH$_2$)$_s$—, where B is —CHR$^1$—, —O—, —S(O)$_m$— or —NR$^{10}$—, m is 0, 1 or 2, and r and s are independently 0 to 3;

R$^{13}$ is selected from the group consisting of: $C_1$–$C_3$ perfluoroalkyl; $C_1$–$C_6$ alkyl; substituted $C_1$–$C_6$ alkyl, where the substitutents on alkyl are hydroxy, NR$^{10}$OR$^{11}$, carboxy, or phenyl; phenyl; and substituted phenyl where the substituents on phenyl are 1 to 3 of halogen, $C_1$–$C_6$ alkyl, $C_1$–$C_6$ alkoxy or hydroxy;

R$^4$, R$^{4b}$, R$^5$ and R$^{5a}$ are independently selected from the group consisting of: hydrogen, phenyl, substituted phenyl, $C_1$–$C_{10}$ alkyl, substituted $C_1$–$C_{10}$ alkyl, $C_3$–$C_{10}$ alkenyl, substituted $C_3$–$C_{10}$ alkenyl, $C_3$–$C_{10}$ alkynyl, or substituted $C_3$–$C_{10}$ alynyl where the substituents on the phenyl, alkyl, alkenyl or alkynyl are selected from:

1 to 5 of hydroxy, $C_1$–$C_6$ alkoxy, $C_3$–$C_7$ cycloalkyl, fluoro, phenyl disubstituted with R$^1$ and R$^2$, $C_1$–$C_3$ alkoxyphenyl disubstituted with R$^1$ and R$^2$, $C_1$–$C_{20}$-alkanoyloxy, $C_1$–$C_5$ alkoxycarbonyl, carboxy, formyl and —NR$^{10}$R$^{11}$ where R$^{10}$ and R$^{11}$ are independently hydrogen, $C_1$–$C_6$ alkyl, phenyl, phenyl $C_1$–$C_6$ alkyl, $C_1$–$C_5$-alkoxycarbonyl or $C_1$–$C_5$-alkanoyl-$C_1$–$C_6$ alkyl;

or R$^4$ and R$^5$ can be taken together to form —CH$_2$)$_r$—B—(CH$_2$)$_s$— where B is CHR$^1$, O, S(O)$_m$ or N—R$^{10}$, r and s are independently 1 to 3;

R$^6$ is selected from the group consisting of: hydrogen, $C_1$–$C_{10}$ alkyl, phenyl and phenyl $C_1$–$C_{10}$ alkyl;

A is:

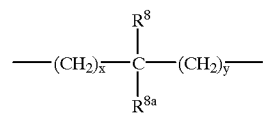

where x and y are independently 0–3;

R$^8$ and R$^{8a}$ are independently selected from the group consisting of: hydrogen, $C_1$–$C_{10}$ alkyl, trifluoromethyl, phenyl, substituted $C_1$–$C_{10}$ alkyl where the substituents on alkyl are selected from:

1 to 3 of imidazolyl, indolyl, hydroxy, fluoro, S(O)$_m$R$^{7a}$, $C_1$–$C_6$ alkoxy, $C_3$–$C_7$ cycloalkyl, phenyl disubstituted with R$^1$ and R$^2$, $C_1$–$C_3$ alkoxy-phenyl disubstituted with R$^1$ and R$^2$, $C_1$–$C_5$-alkanoyloxy, $C_1$–$C_5$ alkoxycarbonyl, carboxy, formyl, and —NR$^{10}$R$^{11}$;

or R$^8$ and R$^{8a}$ can be taken together to form —(CH$_2$)$_t$— where t is 2 to 6; and R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms;

and pharmaceutically acceptable salts and individual diastereomers thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atom fluorine, chlorine, bromine and iodine.

Certain of the above defined terms may occur more than once in the above formula and upon such occurrence each term shall be defined independently of the other.

Preferred compounds of the instant invention include those of Formula I wherein:

n is 0 or 1;

p is 0to 3;

q is 0to 2;

w is 0 or 1;

X is

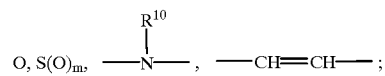

m is 0 to 2;

R$^1$, R$^2$, R$^{1a}$, R$^{2a}$, R$^{1b}$, R$^{2b}$, R$^{1c}$ and R$^{2c}$ are independently selected from the group consisting of: hydrogen, halogen, $C_1$–$C_7$ alkyl, $C_1$–$C_3$ perfluoroalkyl, —S(O)$_m$R$^{7a}$, R$_{7b}$O(CH$_2$)$_v$—, R$^{7b}$COO(CH$_2$)$_v$—, R$^{7b}$OCO(CH$_2$)$_v$—, phenyl or substituted phenyl where the substituents on phenyl are 1 to 3 of halogen, $C_1$–$C_6$ alkyl, $C_1$–$C_6$ alkoxy or hydroxy;

$R^{7a}$ and $R^{7b}$ are independently selected from the group consisting of: hydrogen, $C_1$–$C_3$ perfluoroalkyl, $C_1$–$C_6$ alkyl, $C_1$–$C_6$ alkyl substituted with phenyl, and phenyl;

v is 0 to 2;

$R^{3a}$, $R^{3b}$ and $R^{3c}$ are independently selected from the group consisting of: hydrogen, $R^9$, $C_1$–$C_6$ alkyl substituted with $R^9$, phenyl substituted with $R^9$, or phenoxy substituted with $R^9$ with the proviso that either $R^{3a}$, $R^{3b}$ or $R^{3c}$ must be a substituent other than hydrogen;

$R^9$ is selected from the group consisting of: $R^{4b}R^{12b}NCON(R^{12a})(CH_2)_v$—, $R^{4b}R^{12b}NCSN(R^{12a})(CH_2)_v$—, $R^{4b}R^{12c}NN(R^{12b})CON(R^{12a})(CH_2)_v$—, $R^{4b}R^{12c}NN(R^{12b})COO(CH_2)_v$—, $R^{4b}R^{12b}NCOO(CH_2)_v$— and $R^{13}OCON(R^{12a})(CH_2)_v$—;

$R^{10}$ is hydrogen, $C_1$–$C_6$ alkyl, phenyl $C_1$–$C_6$ alkyl or $C_1$–$C_5$ alkanoyl-$C_1$–$C_6$ alkyl;

$R^{12a}$, $R^{12b}$ and $R^{12c}$ are independently selected from the group consisting of: $R^{5a}$, $OR^{5a}$, or $COR^{5a}$; or $R^{12a}$ and $R^{12b}$ or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form —$(CH_2)_r$—B—$(CH_2)_s$— where B is $CHR^1$, O, $S(O)_m$ or $NR10$, m is 0, 1 or 2, r and s are independently 0 to 3;

$R^{13}$ is selected from the group consisting of: $C_1$–$C_3$ perfluoroalkyl; $C_1$–$C_6$ alkyl; substituted $C_1$–$C_6$ alkyl, where the substitutents on alkyl are hydroxy, $NR^{10}R^{11}$, carboxy, or phenyl; phenyl; and substituted phenyl where the substituents on phenyl are 1 to 3 of halogen, $C_1$–$C_6$ alkyl, $C_1$–$C_6$ alkoxy or hydroxy;

$R^4$, $R^{4b}$, $R^5$ and $R^{5a}$ are independently selected from the group consisting of: hydrogen, phenyl, substituted phenyl, $C_1$–$C_{10}$ alkyl, substituted $C_1$–$C_{10}$ alkyl, $C_3$–$C_{10}$ alkenyl, or substituted $C_3$–$C_{10}$ alkenyl where the substituents on the phenyl, alkyl or alkenyl are selected from:

1 to 5 of hydroxy, $C_1$–$C_6$ alkoxy, $C_3$–$C_7$ cycloalkyl, fluoro, phenyl disubstituted with $R^1$ and $R^2$, $C_1$–$C_3$ alkoxy-phenyl disubstituted with $R^1$ and $R^2$, $C_1$–$C_{20}$-alkanoyloxy, $C_1$–$C_5$ alkoxycarbonyl, carboxy, formyl and —$NR^{10}R^{11}$ where $R^{10}$ and $R^{11}$ are independently hydrogen, $C_1$–$C_6$ alkyl, phenyl, phenyl $C_1$–$C_6$ alkyl, $C_1$–$C_5$-alkoxycarbonyl or $C_1$–$C_5$-alkanoyl-$C_1$–$C_6$ alkyl;

or $R^4$ and $R^5$ can be taken together to form —$(CH_2)_r$—B—$(CH_2)_s$— where B is $CHR^1$, O, $S(O)_m$ or N—$R^{10}$, r and s are independently 1 to 3;

$R^6$ is selected from the group consisting of hydrogen, $C_1$–$C_{10}$ alkyl, phenyl and phenyl $C_1$–$C_{10}$ alkyl;

A is:

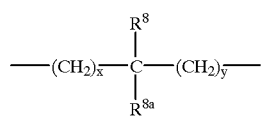

where x and y are independently 0–2;

$R^8$ and $R^{8a}$ are independently selected from the group consisting of: hydrogen, $C_1$–$C_{10}$ alkyl, trifluoromethyl, phenyl, substituted $C_1$–$C_{10}$ alkyl where the substituents on alkyl are selected from:

1 to 3 of imidazolyl, indolyl, hydroxy, fluoro, $S(O)_mR^{7a}$, $C_1$–$C_6$ alkoxy, $C_3$–$C_7$ cycloalkyl, phenyl disubstituted with $R^1$ and $R^2$, $C_1$–$C_3$ alkoxy-phenyl disubstituted with $R^1$ and $R^2$, $C_1$–$C_5$-alkanoyloxy, $C_1$–$C_5$ alkoxycarbonyl, carboxy, formyl, and —$NR^{10}R^{11}$;

or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts and individual diastereomers thereof.

Additional preferred compounds of the instant invention include those of Formula I wherein:

n is 0 or 1;

p is 0 to 2;

q is 0 to 2;

w is 0 or 1;

X is $S(O)_m$ or —CH=CH—;

m is 0 or 1;

$R^1$, $R^2$, $R^{1a}$, $R^{2a}$, $R^{1b}$, $R^{2b}$, $R^{1c}$ and $R^{2c}$ are independently selected from the group consisting of hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the substituents on phenyl are 1 to 3 of halogen, $C_1$–$C_6$ alkyl, $C_1$–$C_6$ alkoxy or hydroxy;

$R^7a$ and $R^{7b}$ are independently selected from the group consisting of: hydrogen, $C_1$–$C_3$ perfluoroalkyl, $C_1$–$C_6$ alkyl, $C_1$–$C_6$ alkyl substituted with phenyl, and phenyl;

v is 0 to 2;

$R^{3a}$, $R^{3b}$ and $R^{3c}$ are independently selected from the group consisting of hydrogen, $R^9$, $C_1$–$C_6$ alkyl substituted with $R^9$, phenyl substituted with $R^9$, or phenoxy substituted with $R^9$ with the proviso that either $R^{3a}$, $R^{3b}$ or $R^{3c}$ must be a substituent other than hydrogen;

$R^9$ is selected from the group consisting of: $R^{4b}R^{12b}NCON(R^{12a})(CH_2)_v$—, $R^{4b}R^{12b}NCSN(R^{12a})(CH_2)_v$—, $R^{4b}R^{12c}NN(R^{12b})CON(R^{12a})(CH_2)_v$—, $R^{4b}R^{12c}NN(R^{12b})COO(CH_2)_v$—, $R^{4b}R^{12b}NCOO(CH_2)_v$— and $R^{13}OCON(R^{12a})(CH_2)_v$—;

$R^{10}$ is hydrogen, $C_1$–$C_6$ alkyl, phenyl $C_1$–$C_6$ alkyl or $C_1$–$C_5$ alkanoyl-$C_1$–$C_6$ alkyl;

$R^{12a}$, $R^{12b}$ and $R^{12c}$ are independently selected from the group consisting of: $R^{5a}$, $OR^{5a}$, or $COR^{5a}$; or $R^{12a}$ and $R^{12b}$, or $R^{12b}$ and $R^{12c}$, or $R^{12a}$ and $R^{12c}$, or $R^{12b}$ and $R^{4b}$, or $R^{12c}$ and $R^{4b}$, or $R^{13}$ and $R^{12a}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3;

$R^{13}$ is selected from the group consisting of. $C_1$–$C_3$ perfluoroalkyl; $C_1$–$C_6$ alkyl; substituted $C_1$–$C_6$ alkyl, where the substitutents on alkyl are hydroxy, $NR^{10}R^{11}$, carboxy, or phenyl; phenyl; and substituted phenyl where the substituents on phenyl are 1 to 3 of halogen, $C_1$–$C_6$ alkyl, $C_1$–$C_6$ alkoxy or hydroxy;

$R^4$, $R^{4b}$, $R^5$ and $R^{5a}$ are independently selected from the group consisting of: hydrogen, $C_1$–$C_{10}$ alkyl, or substituted $C_1$–$C_{10}$ alkyl where the substituents on the alkyl are selected from:

1 to 5 of hydroxy, $C_1$–$C_6$ alkoxy, fluoro, phenyl disubstituted with $R^1$ and $R^2$, $C_1$–$C_{20}$-alkanoyloxy, $C_1$–$C_5$ alkoxycarbonyl, and carboxy; $R^6$ is hydrogen or $C_1$–$C_{10}$ alkyl;

A is:

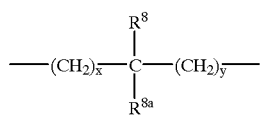

where x and y are independently 0–2;
R$^8$ and R$^{8a}$ are independently selected from the group consisting of: hydrogen, C$_1$–C$_{10}$ alkyl, trifluoromethyl, phenyl, substituted C$_1$–C$_{10}$ alkyl where the substituents on alkyl are selected from:
1 to 3 of imidazolyl, indolyl, hydroxy, fluoro, S(O)$_m$R$^{7a}$, C$_1$–C$_6$ alkoxy, C$_3$–C$_7$ cycloalkyl, phenyl disubstituted with R$^1$ and R$^2$, C$_1$–C$_3$ alkoxy-phenyl disubstituted with R$^1$ and R$^2$, C$_1$–C$_5$-alkanoyloxy, C$_1$–C$_5$ alkoxycarbonyl, carboxy, formyl, and —NR$^{10}$R$^{11}$;
or R$^8$ and R$^{8a}$ can be taken together to form —(CH$_2$)$_t$— where t is 2 to 6; and R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms;
and pharmaceutically acceptable salts and individual diastereomers thereof.

Still further preferred compounds of the instant invention include those of Formula I wherein:
n is 0 or 1;
p is 0 to 2;
q is 1;
w is 1;
X is S(O)$_m$ or —CH=CH—;
m is 0 or 1;
R$^1$, R$^2$, R$^{1a}$, R$^{2a}$, R$^{1b}$, R$^{2b}$, R$^{1c}$ and R$^{2c}$ are independently selected from the group consisting of: hydrogen, halogen, C$_1$–C$_7$ alkyl, C$_1$–C$_3$ perfluoroalkyl, S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents on phenyl are 1 to 3 of halogen, C$_1$–C$_6$ alky, C$_1$–C$_6$ alkoxy or hydroxy;
R$^{7a}$ and R$^{7b}$ are independently selected from the group consisting of: hydrogen, C$_1$–C$_3$ perfluoroalkyl, C$_1$–C$_6$ alkyl, and C$_1$–C$_6$ alkyl substituted with phenyl;
v is 0 or 1;
R$^{3a}$, R$^{3b}$ and R$^{3c}$ are independently selected from the group consisting of: hydrogen, R$^9$, or C$_1$–C$_6$ alkyl substituted with R$^9$, with the proviso that either R$^{3a}$, R$^{3b}$ or R$^{3c}$ must be a substituent other than hydrogen;
R$^9$ is selected from the group consisting of: R$^{4b}$R$^{12b}$NCON (R$^{12a}$)(CH$_2$)$_v$—, R$^{4b}$R$^{12c}$NN(R$^{12b}$)CON(R$^{12a}$)(CH$_2$)$_v$—, R$^{4b}$R$^{12c}$N(R$^{12b}$)COO(CH$_2$)$_v$—, R$^{4b}$R$^{12b}$NCOO(CH$_2$)$_v$— and R$^{13}$OCON(R$^{12a}$)(CH$_2$)$_v$—;
R$^{10}$ is hydrogen, C$_1$–C$_6$ alkyl, phenyl C$_1$–C$_6$ alkyl or C$_1$–C$_5$ alkanoyl-C$_1$–C$_6$ alkyl;
R$^{12a}$, R$^{12b}$ and R$^{12c}$ are independently selected from the group consisting of: R$^{5a}$, OR$^{5a}$, or COR$^{5a}$; or R$^{12a}$ and R$^{12b}$, or R$^{12b}$ and R$^{12c}$, or R$^{12a}$ and R$^{12c}$, or R$^{12b}$ and R$^{4b}$, or R$^{12c}$ and R$^{4b}$, or R$^{13}$ and R$^{12a}$ can be taken together to form —CH$_2$)$_r$—B—(CH$_2$)$_s$— where B is CHR$^1$, O, S(O)$_m$ or NR$^{10}$, m is 0, 1 or 2, r and s are independently 0 to 3;
R$^{13}$ is selected from the group consisting of: C$_1$–C$_6$ alkyl; C$_1$–C$_6$ alkyl substituted with phenyl; phenyl; and substituted phenyl where the substituents on phenyl are 1 to 3 of halogen, C$_1$–C$_6$ alkyl, C$_1$–C$_6$ alkoxy or hydroxy;

R$^4$, R$_{4b}$, R$^5$ and R$^{5a}$ are independently selected from the group consisting of: hydrogen, C$_1$–C$_{10}$ alkyl, or substituted C$_1$–C$_{10}$ alkyl where the substituents on the alkyl are selected from:
1 to 3 of hydroxy, C$_1$–C$_6$ alkoxy, fluoro, phenyl disubstituted with R$^1$ and R$^2$, C$_1$–C$_{20}$-alkanoyloxy, C$_1$–C$_5$ alkoxycarbonyl, and carboxy;
R$^6$ is hydrogen;
A is:

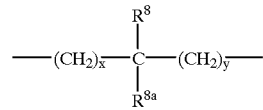

where x and y are independently 0–1;
R$^8$ and R$^{8a}$ are independently selected from the group consisting of: hydrogen, C$_1$–C$_{10}$ alkyl, trifluoromethyl, substituted C$_1$–C$_{10}$ alkyl where the substituents on alkyl are selected from:
1 to 3 of imidazolyl, indolyl, hydroxy, fluoro, S(O)$_m$R$^{7a}$, C$_1$–C$_6$ alkoxy, C$_3$–C$_7$ cycloalkyl, phenyl disubstituted with R$^1$ and R$^2$, C$_1$–C$_3$ alkoxy-phenyl disubstituted with R$^1$ and R$^2$, C$_1$–C$_5$-alkanoyloxy, C$_1$–C$_5$ alkoxycarbonyl and carboxy;
or R$^8$ and R$^{8a}$ can be taken together to form —CH$_2$)$_t$— where t is 2; and R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms;
and pharmaceutically acceptable salts and individual diastereomers thereof.

Representative preferred compounds of the present invention include the following:

1. 2-Amino-2-methyl-N-[3(R)-2,3,4,5-tetrahydro-5-[[2'-[[[(methylamino)carbonyl]amino]methyl][1,1'-biphenyl]-4-yl]methyl]-4-oxo-1H-naphtho[2,1-b]azepin-3(R)-yl]propanamide;
2. 3-Amino-3-methyl-N-[3(R)-2,3,4,5-tetrahydro-5-[[2'-[[[(methylamino)carbonyl]amino]methyl][1,1'-biphenyl]-4-yl]methyl]-4-oxo-1H-naphtho[2,1-b]-3(R)-yl]butanamide;
3. 3-[2(R)-Hydroxypropyl]amino-3-methyl-N-[3(R)-2,3,4,5-tetrahydro-5-[[2'-[[[(methylamino)carbonyl]amino]methyl][1,1'-biphenyl]-4-yl]-methyl]-4-oxo-1H-naphtho[2,1-b]-3(R)-yl]butanamide;
4. 3-[2(S),3-Dihydroxypropyl]amino-3-methyl-N-[2,3,4,5-tetra-hydro-1-[[2'-[[[(methylamino)carbonyl]amino]methyl][1,1'-biphenyl]-4-yl]methyl]-4-oxo-1H-naphtho[2,1-b]azepin-3(R)-yl]butanamide;
5. 2-Amino-2-methyl-N-[3(R)-2,3,4,5-tetrahydro-5-[[2'-[[(aminocarbonyl)amino]methyl][1,1'-biphenyl]-4-yl]methyl]-4-oxo-1H-naphtho[2,1-b]azepin-3(R)-yl]propanamide;
6. 3-Amino-3-methyl-N-[3(R)-2,3,4,5-tetrahydro-5-[[2'-[[(aminocarbonyl)amino]methyl][1,1'-biphenyl]4-yl]methyl]-4-oxo-1H-naphtho[2,1-b]azepin-3(R)-yl]butanamide;
7. 3-[2(R)-Hydroxypropyl]amino-3-methyl-N-[3(R)-2,3,4,5-tetrahydro-5-[[2'-[[(aminocarbonyl)amino]methyl][1,1'-biphenyl]-4-yl]methyl]-4-oxo-1H-naphtho[2,1-b]azepin-3(R)-yl]butanamide;
8. 3-[2(S),3-Dihydroxypropyl]amino-3-methyl-N-[2,3,4,5-tetra-hydro-1-[[2'-[[(aminocarbonyl)amino]methyl][1,1'-biphenyl]-4-yl]methyl]-4-oxo-1H-naphtho[2,1-b]azepin-3(R)-yl]butanamide;

9. 2-Amino-2-methyl-N-[3(R)-2,3,4,5-tetrahydro-5-[[2'-[[[(ethylamino)carbonyl]amino]methyl][1,1'-biphenyl]-4-yl]methyl]-4-oxo-1H-naphtho[2,1-b]azepin-3(R)-yl]propanamide;
10. 3-Amino-3-methyl-N-[3(R)-2,3,4,5-tetrahydro-5-[[2'-[[[(ethylamino)carbonyl]amino]methyl][1,1'-biphenyl]-4-yl]methyl]-4-oxo-1H-naphtho[2,1-b]azepin-3(R)-yl]butanamide;
11. 3-[2(R)-Hydroxypropyl]amino-3-methyl-N-[3(R)-2,3,4,5-tetrahydro-5-[[2'-[[[(ethylamino)carbonyl]amino]methyl][1,1'-biphenyl]-4-yl]-methyl]-4-oxo-1H-naphtho[2,1-b]azepin-3(R)-yl]butanamide;
12. 3-[2(S),3-Dihydroxypropyl]amino-3-methyl-N-[2,3,4,5-tetra-hydro-1-[[2'-[[[(ethylamino)carbonyl)amino]methyl][1,1'-biphenyl]-4-yl]methyl]-4-oxo-1H-naphtho[2,1-b]azepin-3(R)-yl]butanamide;
13. 2-Amino-2-methyl-N-[3(R)-2,3,4,5-tetrahydro-5-[[2'-[[[[(hydroxyethyl)amino]carbonyl]amino]methyl][1,1'-biphenyl]-4-yl]methyl]-4-oxo-1H-naphtho[2,1-b]azepin-3(R)-yl]propanamide;
14. 3-Amino-3-methyl-N-[3(R)-2,3,4,5-tetrahydro-5-[[2'-[[[[(hydroxyethyl)amino]carbonyl]amino]methyl][1,1'-biphenyl]-4-yl]methyl]-4-oxo-1H-naphtho[2,1-b]azepin-3(R)-yl]butanamide;
15. 3-[2(R)-Hydroxypropyl]amino-3-methyl-N-[3(R)-2,3,4,5-tetrahydro-5-[[2'-[[[[(hydroxyethyl)amino]carbonyl]amino]methyl][1,1'-biphenyl]-4-yl]methyl]-4-oxo-1H-naphtho[2,1-b]azepin-3(R)-yl]butanamide;
16. 3-[2(S),3-Dihydroxypropyl]amino-3-methyl-N-[2,3,4,5-tetra-hydro-1-[[2'-[[[[(hydroxyethyl)amino]carbonyl]amino]methyl]-[1,1'-biphenyl]-4-yl]methyl]-4-oxo-1H-naphtho[2,1-b]azepin-3(R)-yl]butanamide;
17. 2-Amino-2-methyl-N-[3(S)-2,3,4,5-tetrahydro-5-[[2'-[[[(methylamino)-carbonyl]amino]methyl][1,1'-biphenyl]-4-yl]methyl]-4-oxonaphtho[1,2-b][1,4]thiazepin-3-yl]propanamide;
18. 3-Amino-3-methyl-N-[3(S)-2,3,4,5-tetrahydro-5-[[2'-[[[(methylamino)-carbonyl]amino]methyl][1,1'-biphenyl]-4-yl]methyl]-4-oxonaphtho[1,2-b][1,4]thiazepin-3-yl]butanamide;
19. 3-[2(R)-Hydroxypropyl]amino-3-methyl-N-[3(S)-2,3,4,5-tetrahydro-5-[[2'-[[[(methylamino)carbonyl]amino]methyl][1,1'-biphenyl]-4-yl]-methyl]-4-oxonaphtho[1,2-b][1,4]thiazepin-3-yl]butanamide;
20. 3-[2(S),3-Dihydroxypropyl]amino-3-methyl-N-[3(S)-2,3,4,5-tetrahydro-5-[[2'-[[[(methylamino)carbonyl]amino]methyl][1,1'-biphenyl]-4-yl]methyl]-4-oxonaphtho[1,2-b][1,4]thiazepin-3-yl]-butanamide;
21. 2-Amino-2-methyl-N-[3(S)-2,3,4,5-tetrahydro-1-[[2'-[[(aminocarbonyl)amino]methyl][1,1'-biphenyl]-4-yl]methyl]-4-oxonaphtho[1,2-b][1,4]thiazepin-3-yl]propanamide;
22. 3-Amino-3-methyl-N-[3(S)-2,3,4,5-tetrahydro-5-[[2'-[[(aminocarbonyl)amino]methyl][1,1'-biphenyl]-4-yl]methyl]-4-oxonaphtho[1,2-b][1,4]thiazepin-3-yl]butanamide;
23. 3-[2(R)-Hydroxypropyl]amino-3-methyl-N-[3(S)-2,3,4,5-tetrahydro-5-[[2'-[[(aminocarbonyl)amino]methyl][1,1'-biphenyl]-4-yl]methyl]-4-oxonaphtho[1,2-b][1,4]thiazepin-3-yl]butanamide;
24. 3-[2(S),3-Dihydroxypropyl]amino-3-methyl-N-[3(S)-2,3,4,5-tetrahydro-5-[[2'-[[(aminocarbonyl)amino]methyl][1,1'-biphenyl]-4-yl]methyl]-4-oxonaphtho[1,2-b][1,4]thiazepin-3-yl]butanamide;
25. 2-Amino-2-methyl-N-[3(S)-2,3,4,5-tetrahydro-5-[[2'-[[[(ethylamino)-carbonyl]amino]methyl][1,1'-biphenyl]-4-yl]methyl]-4-oxonaphtho[1,2-b][1,4]thiazepin-3-yl]propanamide;
26. 3-Amino-3-methyl-N-[3(S)-2,3,4,5-tetrahydro-5-[[2'-[[[(ethylamino)-carbonyl]amino]methyl][1,1'-biphenyl]-4-yl]methyl]-4-oxonaphtho[1,2-b][1,4]thiazepin-3-yl]butanamide;
27. 3-[2(R)-Hydroxypropyl]amino-3-methyl-N-[3(S)-2,3,4,5-tetrahydro-5-[[2'-[[[(ethylamino)carbonyl]amino]methyl][1,1'-biphenyl]-4-yl]-methyl]-4-oxonaphtho1,2-b][1,4]thiazepin-3-yl]butanamide;
28. 3-[2(S),3-Dihydroxypropyl]amino-3-methyl-N-[3(S)-2,3,4,5-tetrahydro-5-[[2'-[[[(ethylamino)carbonyl]amino]methyl][1,1'-biphenyl]-4-yl]methyl]-4-oxonaphtho[1,2-b][1,4]thiazepin-3-yl]-butanamide;
29. 2-Amino-2-methyl-N-[3(S)-2,3,4,5-tetrahydro-5-[[2'-[[[[(hydroxyethyl)amino]carbonyl]amino]methyl][1,1'-biphenyl]-4-yl]methyl]-4-oxonaphtho[1,2-b][1,4]thiazepin-3-yl]propanamide;
30. 3-Amino-3-methyl-N-[3(S)-2,3,4,5-tetrahydro-5-[[2'-[[[[(hydroxyethyl)amino]carbonyl]amino]methyl][1,1'-biphenyl]-4-yl]methyl]-4-oxonaphtho[1,2-b][1,4]thiazepin-3-yl]butanamide;
31. 3-[2(R)-Hydroxypropyl]amino-3-methyl-N-[3(S)-2,3,4,5-tetrahydro-5-[[2'-[[[[(hydroxyethyl)amino]carbonyl]amino3-methyl][1,1'-biphenyl]-4yl]methyl]-4-oxonaphtho[1,2-b][1,4]thiazepin-3-yl]-butanamide;
32. 3-[2(S),3-Dihydroxypropyl]amino-3-methyl-N-[3(S)-2,3,4,5-tetrahydro-5-[[2'-[[[[(hydroxyethyl)amino]carbonyl]amino]-methyl]-[1,1'-biphenyl]-4-yl]methyl]-4-oxonaphtho[1,2-b][1,4]thiazepin-3-yl]butanamide;
33. 2-Amino-2-methyl-N-[3(R)-2,3,4,5-tetrahydro-5-[[2'-[2-[[(methylamino)carbonyl]amino]prop-2-yl][1,1'-biphenyl]-4-yl]methyl]-4-oxo-1H-naphtho[2,1-b]azepin-3(R)-yl]propanamide;
34. 2-Amino-2-methyl-N-[3(R)-2,3,4,5-tetrahydro-5-[[2'-[1-[[(methylamino)carbonyl]amino]ethyl][1,1'-biphenyl]-4-yl]methyl]-4-oxo-1H-naphtho[2,1-b]azepin-3(R)-yl]propanamide;
35. 2-Amino-2-methyl-N-[3(R)-2,3,4,5-tetrahydro-5-[[2'-[[(methoxycarbonyl)amino]methyl][1,1'-biphenyl]-4-yl]methyl]-4-oxo-1H-naphtho[2,1-b]azepin-3(R)-yl]propanamide;
36. 3-Amino-3-methyl-N-[3(R)-2,3,4,5-tetrahydro-5-[[2'-[[(methoxycarbonyl)amino]methyl][1,1'-biphenyl]-4-yl]methyl]-4-oxo-1H-naphtho[2,1-b]azepin-3(R)-yl]butanamide;
37. 3-[2(R)-Hydroxypropyl]amino-3-methyl-N-[3(R)-2,3,4,5-tetrahydro-5-[[2'-[[(methoxycarbonyl)amino]methyl][1,1'-biphenyl]-4-yl]-methyl]-4-oxo-1H-naphtho[2,1-b]azepin-3(R)-yl]butanamide;
38. 3-[2(S),3-Dihydroxypropyl]amino-3-methyl-N-[2,3,4,5-tetra-hydro-1-[[2'-[[(methoxycarbonyl)amino]methyl][1,1'-biphenyl]-4-yl]methyl]-4-oxo-1H-naphtho[2,1-b]azepin-3(R)-yl]butanamide;
39. 2-Amino-2-methyl-N-[3(S)-2,3,4,5-tetrahydro-5-[[2'-[[(methoxycarbonyl)amino]methyl][1,1'-biphenyl]-4-yl]methyl]-4-oxonaphtho[1,2-b][1,4]thiazepin-3-yl]propanamide;
40. 3-Amino-3-methyl-N-[3(S)-2,3,4,5-tetrahydro-5-[[2'-[[(methoxycarbonyl)amino]methyl][1,1'-biphenyl]-4-yl]methyl]-4-oxonaphtho[1,2-b][1,4]thiazepin-3-yl]butanamide;
41. 3-[2(R)-Hydroxypropyl]amino-3-methyl-N-[3(S)-2,3,4,5-tetrahydro-5-[[2'-[[(methoxycarbonyl)amino]methyl][1,1'-biphenyl]-4-yl]-methyl]-4-oxonaphtho[1,2-b][1,4]thiazepin-3-yl]butanamide;
42. 3-[2(S),3-Dihydroxypropyl]amino-3-methyl-N-[3(S)-2,3,4,5-tetrahydro-5-[[2'-[[(methoxycarbonyl)amino]methyl][1,1'-biphenyl]-4-yl]methyl]-4-oxonaphtho1,2-b][1,4]thiazepin-3-yl]butanamide;

43. 2-Amino-2-methyl-N-[3(R)-2,3,4,5-tetrahydro-5-[[2'-[[[(methylamino)-carbonyl]oxy]methyl][1,1'-biphenyl]-4-yl]methyl]-4-oxo-1H-naphtho[2,1-b]azepin-3(R)-yl]propanamide;

44. 3-Amino-3-methyl-N-[3(R)-2,3,4,5-tetrahydro-5-[[2'-[[[(methylamino)-carbonyl]oxy]methyl][1,1'-biphenyl]-4-yl]methyl]-4-oxo-1H-naphtho[2,1-b]azepin-3(R)-yl]butanamide;

45. 3-[2(R)-Hydroxrypropyl]amino-3-methyl-N-[3(R)-2,3,4,5-tetrahydro-5-[[2'-[[[(methylamino)carbonyl]oxylmethyl][1,1'-biphenyl]-4-yl]-methyl]-4-oxo-1H-naphtho[2,1-b]azepin-3(R)-yl]butanamide;

46. 3-[2(S),3-Dihydroxypropyl]amino-3-methyl-N-[2,3,4,5-tetra-hydro-1-[[2'-[[[(methylamino)carbonyl]oxy]methyl][1,1'-biphenyl]-4-yl]methyl]-4-oxo-1H-naphtho[2,1-b]azepin-3(R)-yl]butanamide;

47. 2-Amino-2-methyl-N-[3(S)-2,3,4,5-tetrahydro-5-[[2'-[[[(methylamino)-carbonyl]oxy]methyl][1,1'-biphenyl]-4-yl]methyl]-4-oxonaphtho[1,2-b][1,4]thiazepin-3-yl]propanamide;

48. 3-Amino-3-methyl-N-[3(S)-2,3,4,5-tetrahydro-5-[[2'-[[[(methylamino)-carbonyl]oxy]methyl][1,1'-biphenyl]-4-yl]methyl]-4-oxonaphtho[1,2-b][1,4]thiazepin-3-yl]butanamide;

49. 3-[2(R)-Hydroxypropyl]amino-3-methyl-N-[3(S)-2,3,4,5-tetrahydro-5-[[2'-[[[(methylamino)carbonyl]oxy]methyl][1,1'-biphenyl]-4-yl]-methyl]-4-oxonaphtho[1,2-b][1,4]thiazepin-3-yl]butanamide;

50. 3-[2(S),3-Dihydroxypropyl]amino-3-methyl-N-[3(S)-2,3,4,5-tetrahydro-5-[[2'-[[[(methylamino)carbonyl]oxy]methyl][1,1'-biphenyl]-4-yl]methyl]-4-oxonaphtho1,2-b][1,4]thiazepin-3-yl]-butanamide.

51. 2-Amino-2-methyl-N-[3(S)-2,3,4,5-tetrahydro-5-[[2'-[[[(methylamino)-carbonyl]amino]methyl][1,1'-biphenyl]-4-yl]methyl]-4-oxonaphtho[1,2-b][1,4]oxazepin-3-yl]propanamide;

52. 3-Amino-3-methyl-N-[3(S)-2,3,4,5-tetrahydro-5-[[2'-[[[(methylamino)-carbonyl]amino]methyl][1,1'-biphenyl]-4-yl]methyl]-4-oxonaphtho[1,2-b][1,4]oxazepin-3-yl]butanamide;

and pharmaceutically acceptable salts and individual diastereomers thereof.

Representative examples of the nomenclature employed are given below:

2-Amino-2-methyl-N-[3(R)-2,3,4,5-tetrahydro-5-[[2'-[[[(methylamino)carbonyl]amino]methyl][1,1'-biphenyl]-4-yl]methyl]-4oxo-1H-naphtho[2,1-b]azepin-3-yl]propanamide;

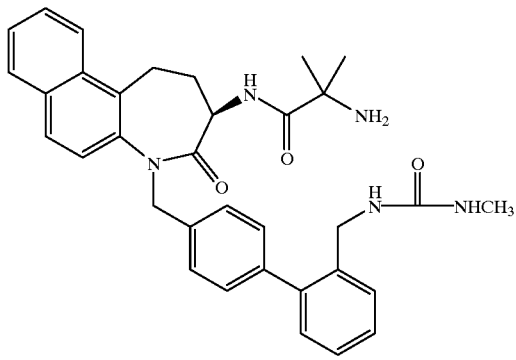

2-Amino-2-methyl-N-[3(S)-2,3,4,5-tetrahydro-5-[[2'-[[[(methylamino)-carbonyl]amino]methyl][1,1'-biphenyl]-4-yl]methyl]-4-oxonaphtho[1,2-b][1,4]thiazepin-3-yl]propanamide;

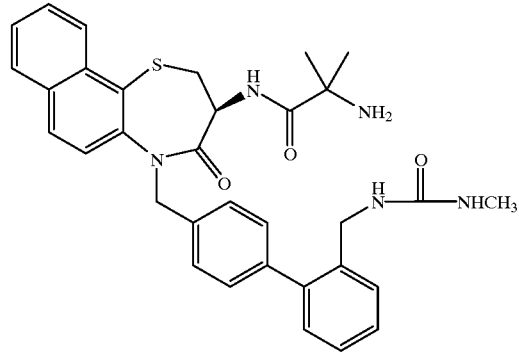

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. In the substituent $(X)_n$, when n=0, the asymmetric center is designated as the R-isomer. When n=1, this center will be designated according to the R/S rules as either R or S depending upon the value of X.

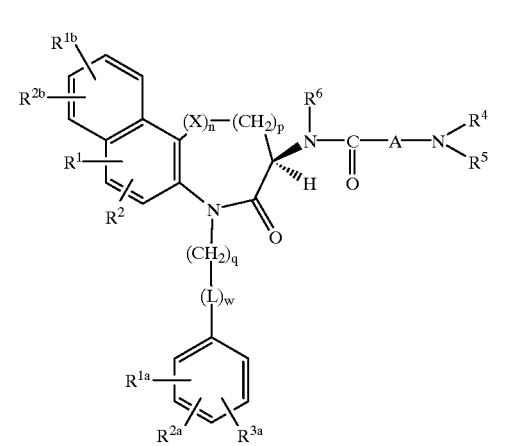

Ia

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The compounds (I) of the present invention are prepared from aminolactam intermediates such as those of formula II.

The preparation of these intermediates is described in the following Reaction Schemes.

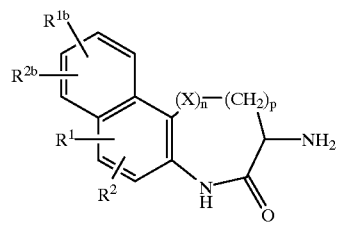

II

Conversion of substituted naphtho-fused lactams to the requisite 3-amino derivatives may be achieved by a number of methods familiar to those skilled in the art (such as those described in PCT Publication WO 96/05195 and references cited therein). One common route proceeds via the intermediacy of a 3-halo (chloro, bromo or iodo) intermediate which is subsequently displaced by a nitrogen nucleophile, typically azide.

Chiral aminonaphtholactams are obtained by resolution of the racemates by classical methods familiar to those skilled in the art (such as described in PCT Publication WO 96/05195). For example, resolution can be achieved by formation of diastereomeric salts of the racemic amines with optically active acids such as D- and L-tartaric acid. Determination of absolute stereochemistry can be achieved in a number of ways including X-ray analysis of a suitable crystalline derivative.

Alternatively, chiral aminonaphtholactams are obtained by racemization/resolution according to the procedure of J. A. Armstrong III et al. Tetrahedron Letters 35 p3239–3242 (1994). For example, resolution can be achieved by treatment of the racemic amines with optically active acids such as D- and L-tartaric acid and 5-nitro-salicylaldehyde in an appropriate solvent such as isopropanol and water or other alcoholic solvents with or without water at or above room temperature.

SCHEME 1

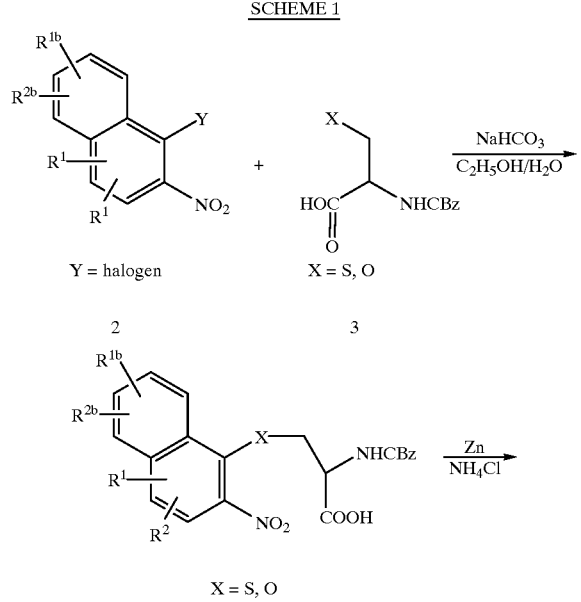

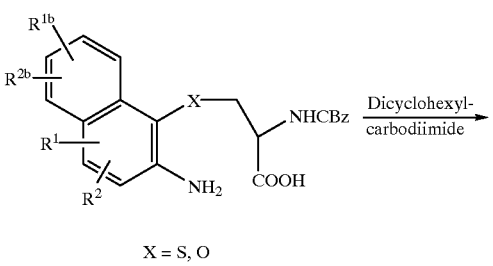

X = S, O

5

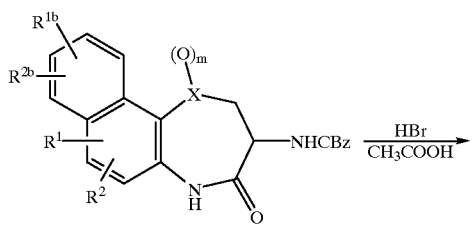

6 X = S; m = 0, 7 X = S; m = 1,
8 X = S; m = 2, 9 X = O; m = 0,

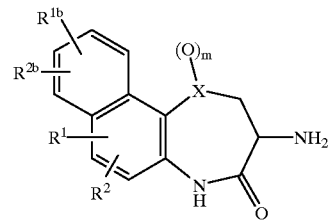

10 X = S; m = 0, 11 X = S; m = 1,
12 X = S; m = 2, 13 X = O; m = 0

Intermediates of Formula II wherein X is a sulfur atom are prepared by methods described in the literature and known to those skilled in the art. As illustrated in the Scheme 1, the seven-membered ring analog is prepared from a protected derivative of cysteine and halonitronaphthalene (for example, 1-fluoro-2-nitronaphthalene prepared by the method of Bassilios et. al, Bull. Chim. Soc. Belges 75, 577–581 (1966)) by the method of Slade, et al, J. Med. Chem., 28. 1517–1521 (1985) for the benzothiazepinone and references cited therein (CBZ is benzyloxycarbonyl). Similarly, interemediates of Formula II wherein X is an oxygen atom are prepared using the same reaction sequence for a protected serine derivative and the halonitronaphthalene.

Sulfoxide and sulfone intermediates 36 and 37 are prepared by oxidation of 32 with various oxidants such as sodium periodate or meta-chloroperbenzoic acid. Eight-membered ring intermediates of Formula II wherein X is sulfur or oxygen can be prepared by an analogous route starting from derivatives of homo-cysteine or homo-serine.

SCHEME 2

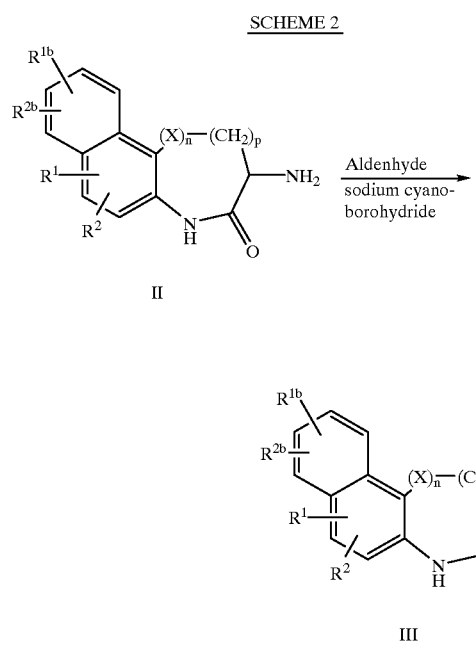

Intermediates of formula II can be further elaborated to new intermediates (formula III) which are substituted on the amino group (Scheme 2). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

SCHEME 3

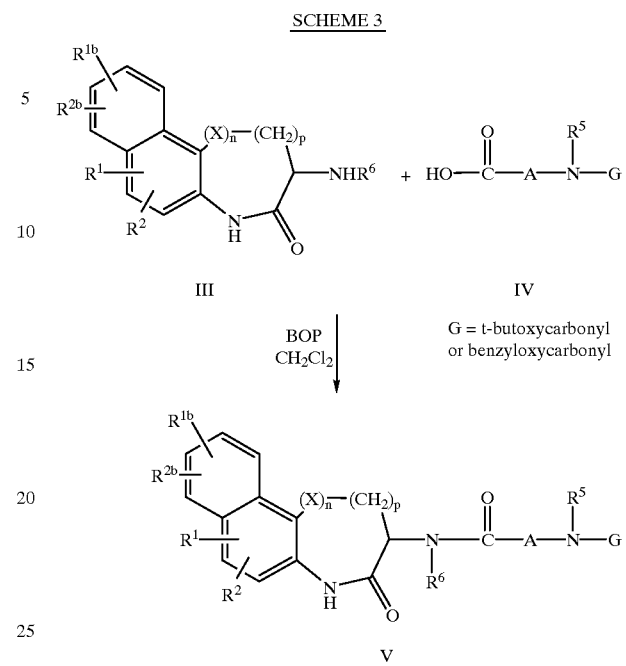

Attachment of the amino acid sidechain to intermediates of formula III is accomplished by the route shown in Scheme 3. Coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP") or benzotriazol-1-yloxytripyrrolidinophosphonium hexafluorophosphate ("PyBOP") in an inert solvent such as methylene chloride. Separation of unwanted side products, and purification of intermediates is achieved by chromatography on silica gel, employing flash chromatography (W. C. Still, M. Kahn and A. Mitra, J. Org. Chem., 43, 2923 (1978)) or by medium pressure liquid chromatography.

SCHEME 4

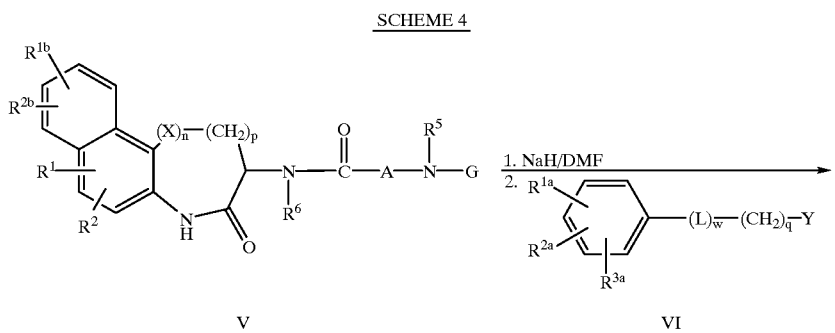

-continued

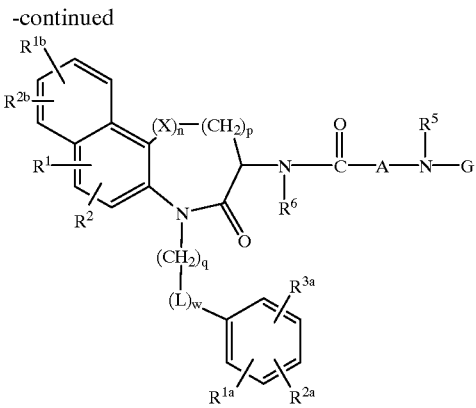

VII

Y is a leaving group
G is t-butoxycarbonyl or benzloxycarbonyl

The protected amino acid derivatives IV are, in many cases, commercially available in t-butoxycarbonyl (BOC) or benzyloxy-carbonyl (CBz) forms. A useful method to prepare the preferred sidechain 3-N-t-butoxycarbonylamino-3-methylbutanoic acid is described in U.S. Pat. No. 5,206,235.

Intermediates of formula VII are prepared as shown in Scheme 4 by treatment of the desired lactam intermediate V with an alkylating agent VI, wherein Y is a good leaving group such as Cl, Br, I, O-methanesulfonyl or O-(p-toluenesulfonyl). Alkylation of intermediates of formula V is conveniently carried out in anhydrous dimethyl formamide (DMF) in the presence of bases such as sodium hydride or potassium t-butoxide for a period of 0.5 to 24 hours at temperatures of 20–100° C. Substituents on the alkylating agent VI may need to be protected during alkylation. A description of such protecting groups may be found in: Protective Groups in Organic Synthesis, T. W. Greene, John Wiley and Sons, New York, 1981.

SCHEME 5

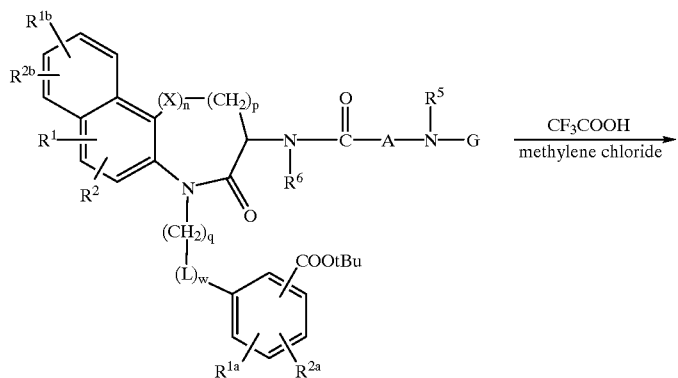

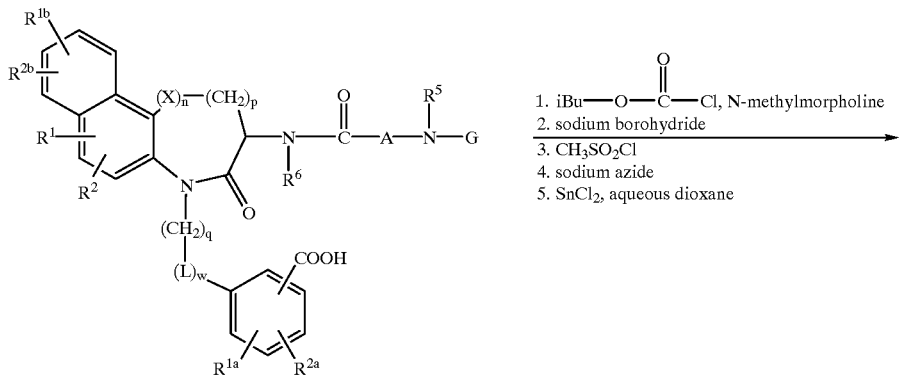

15

G is benzyloxycarbonyl 1. iBu—O—C(=O)—Cl, N-methylmorpholine
2. sodium borohydride
3. CH$_3$SO$_2$Cl
4. sodium azide
5. SnCl$_2$, aqueous dioxane

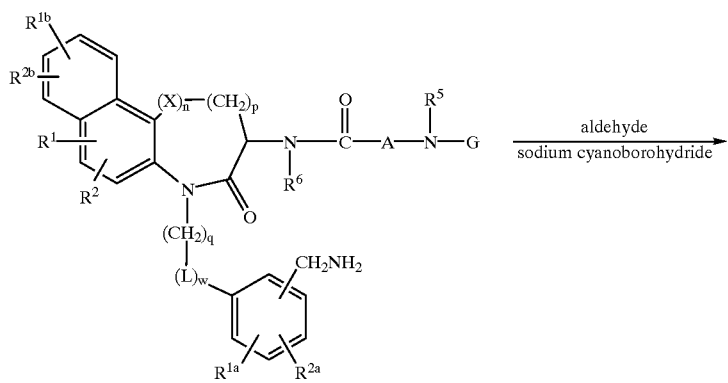

16

G is benzyloxycarbonyl aldehyde / sodium cyanoborohydride

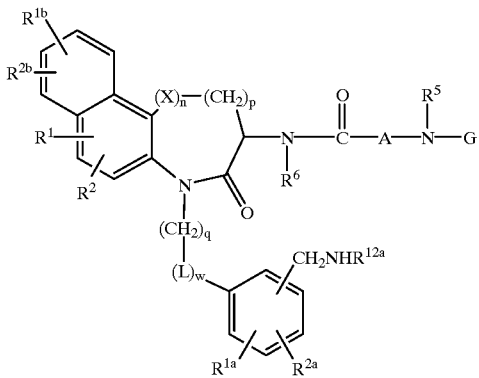

17

G is benzyloxycarbonyl

Compounds of formula I wherein $R^{3a}$, $R^{3b}$ or $R^{3c}$ is $R^{4b}R^{12b}NCON(R^{12a})CH_2$—, $R^{4b}R^{12b}NCSN(R^{12a})CH_2$—, $R^{4b}R^{12c}NN(R^{12b})CSN(R^{12a})CH_2$—, $R^{4b}R^{12c}NN(R^{12b})CON(R^{12a})CH_2$— or $R^{13}OCON(R^{12a})CH_2$— can be prepared from the t-butyl ester intermediate 14 as described in Scheme 5. Removal of the t-butyl ester through the use of trifluoroacetic acid will give the carboxylic acid 15. It may be appreciated by one skilled in the art that the protecting group G in 14 must therefore be compatible with the strongly acidic conditions employed for ester cleavage; hence G is taken as benzyloxycarbonyl. Conversion of the carboxylic acid to the benzylamine derivative 16 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 16 can be further elaborated to 17 by the aforementioned reductive amination procedure.

SCHEME 6
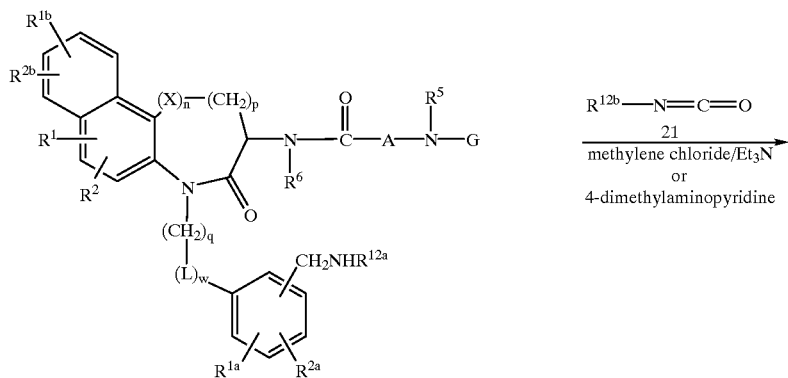
17
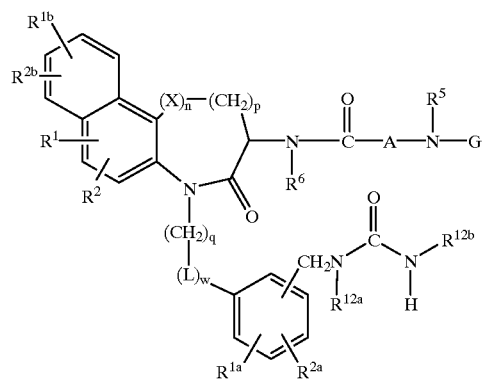
18
G is benzyloxycarbonyl
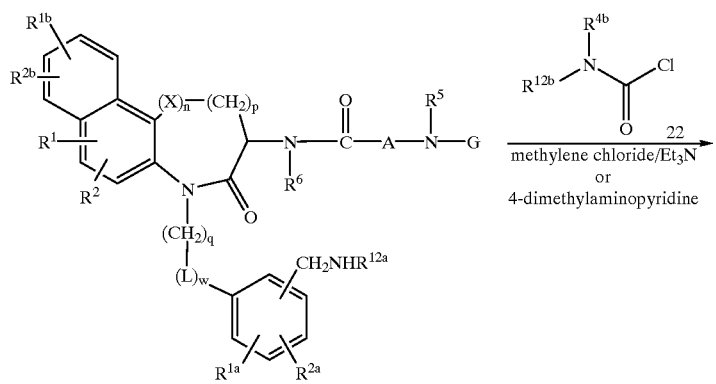
17

-continued
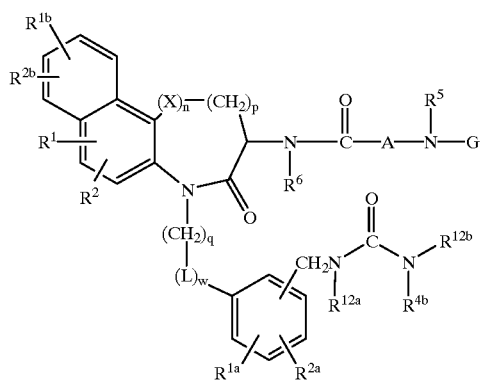
19
G is benzyloxycarbonyl
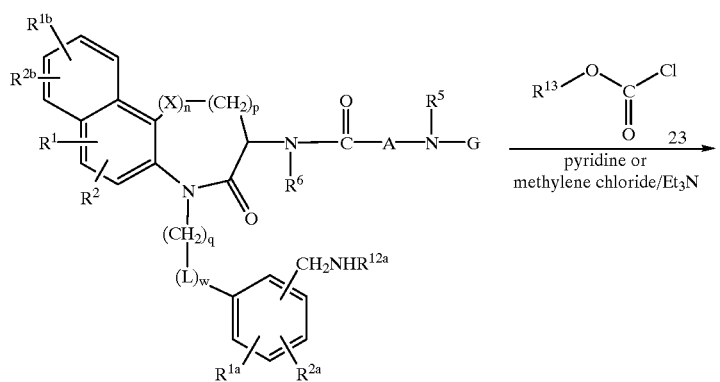
17
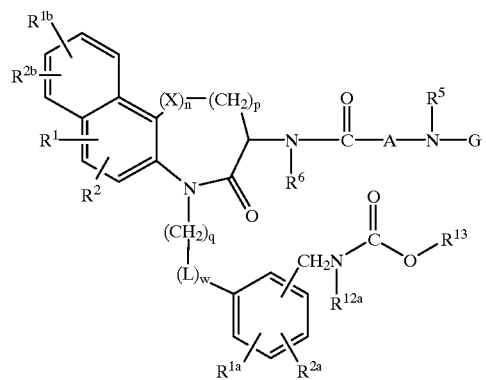
20
G is benzyloxycarbonyl
Reactions of amine 17 with the appropriate reagents to form urea-linked compounds 18 and 19 and carbamate-linked compound 20 are illustrated in Scheme 6. Terminally unsubstituted urea 18, wherein $R^{12b}$ is hydrogen, is also prepared from amine 17 by reaction with trimethylsilyl isocyanate (60; $R^{12b}$ is $(CH_3)_3Si$).

SCHEME 7
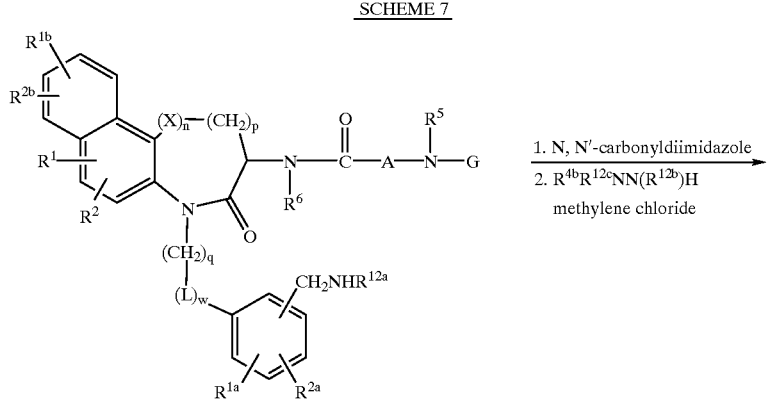
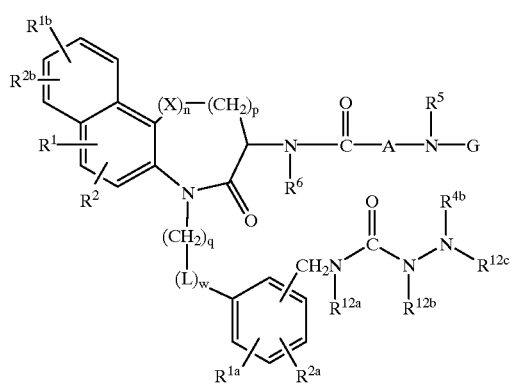
G is benzyloxycarbonyl
As shown in Scheme 7, hydrazide compound 24 can be prepared from intermediate 17 by a two-step procedure consisting of activation of the amine via treatment with N,N'-carbonyldiimidazole followed by treatment with the appropriately substituted hydrazine derivative $R^{4b}R^{12c}NN(R^{12b})H$.
SCHEME 8
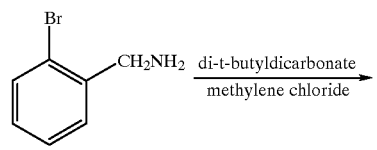
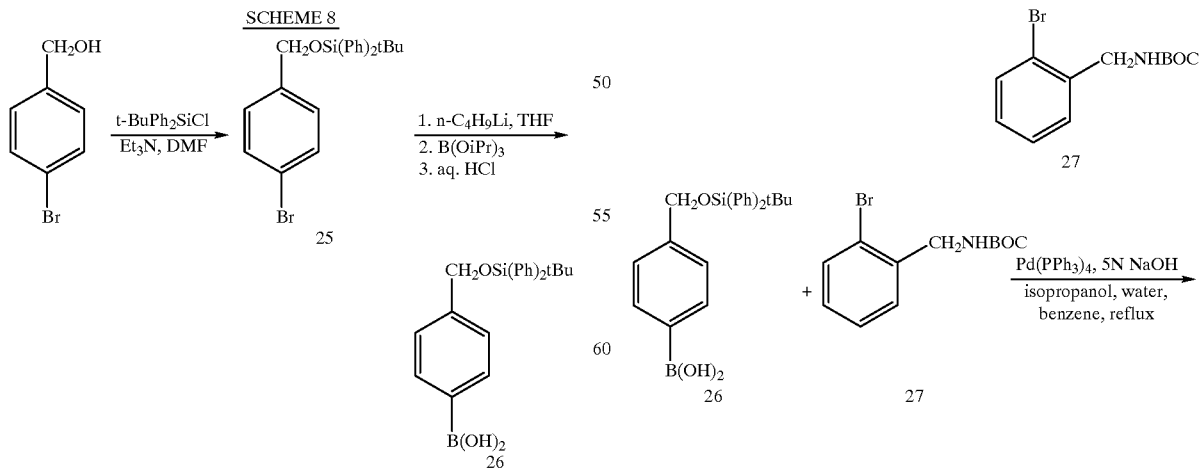

-continued

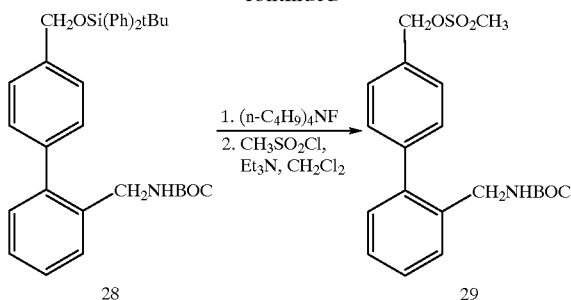

A useful preparation of the protected benzylamine intermediate 30 is shown in Scheme 8. Metallation of 4-bromobenzyl t-butyldiphenylsilylether 25 with n-butyllithiuim followed by treatment with triisopropyl borate gives the aryl boronic acid 26. Reaction of 26 with 2-bromo-N-(t-butoxycarbonyl)benzylamine 27 in the presence of tetrakis(triphenylphosphine)palladium(0) and sodium hydroxide in a mixed solvent system at elevated temperature gives the coupled product 28 in good yield. Desilylation and conversion to the O-methanesulfonate 29 is achieved by treatment with tetrabutylammonium fluoride followed by methanesulfonyl chloride. Reaction of 29 with compounds of formula V is carried out using the conditions described in Scheme 4.

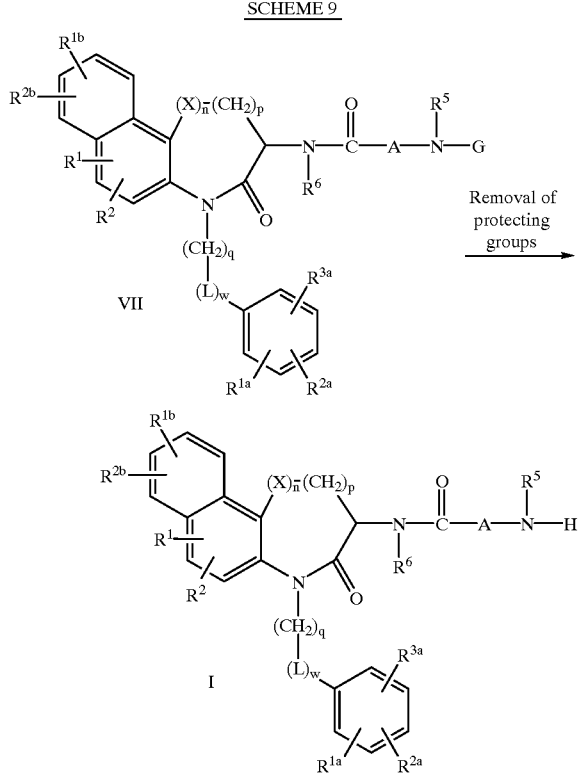

Conversion to the final products of formula I wherein $R^4$ is hydrogen, is carried out by simultaneous or sequential removal of all protecting groups from intermediate VII as illustrated in Scheme 9.

Removal of benzyloxycarbonyl (CBz) groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in Protective Groups in Organic Synthesis T. W. Greene, John Wiley and Sons, New York 1981.

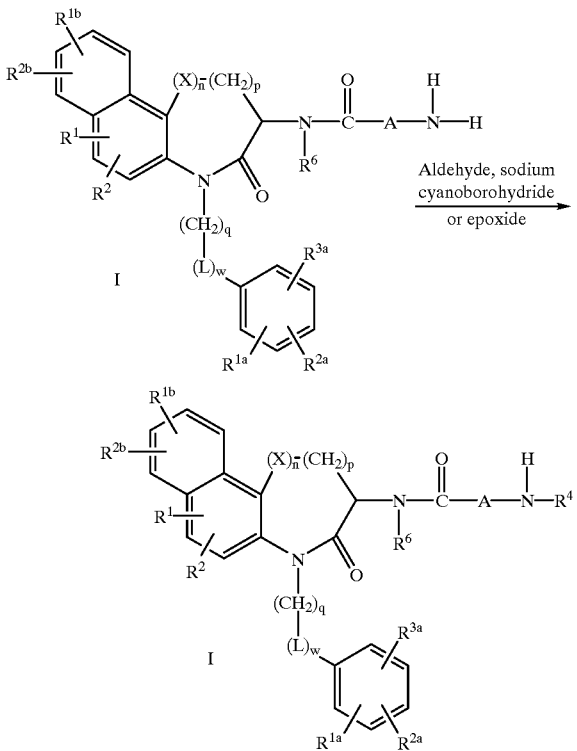

As shown in Scheme 10, compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatography (HPLC) or by recrystallization.

It is noted that the order of carrying out the foregoing reaction schemes is not significant and it is within the skill of one skilled in the art to vary the order of reactions to facilitate the reaction or to avoid unwanted reaction products. In some cases the order of carrying out the foregoing reaction schemes may be varied to facilitate the reaction or to avoid unwanted reaction products.

The utility of the compounds of the present invention as growth hormone secretagogues may be demonstrated by methodology known in the art, such as an assay disclosed by Smith, et al., Science, 260, 1640–1643 (1993) (see text of FIG. 2 therein). In particular, all of the compounds prepared in the following examples had activity as growth hormone secretagogues in the aforementioned assay. Such a result is indicative of the intrinsic activity of the present compounds as growth hormone secretagogues.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive peptides, e.g., bombesin, the neurokinins; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, to improve feed efficiency and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise an anabolic agent in addition to at least one of the compounds of Formula I or another composition which exhibits a different activity, e.g., an antibiotic growth permittant or an agent to treat osteoporosis or in combination with a corticosteroid to minimize the latter's catabolic side effects or with other pharmaceutically active materials wherein the combination enhances efficacy and minimizes side effects.

Growth promoting and anabolic agents include, but are not limited to, TRH, diethylstilbesterol, amino acids, estrogens, b-agonists, theophylline, anabolic steroids, enkephalins, E series prostaglandins, retinoic acid, compounds disclosed in U.S. Pat. No. 3,239,345, e.g., zeranol, and compounds disclosed in U.S. Pat. No. 4,036,979, e.g., sulbenox, or peptides disclosed in U.S. Pat. No. 4,411,890.

A still further use of the compounds of this invention is in combination with other growth hormone secretagogues such as the growth hormone releasing peptides GHRP-6, GHRP-1 as described in U.S. Pat. Nos. 4,411,890 and publications WO 89/07110, WO 89/07111 and B-HT920 as well as hexarelin and GHRP-2 as described in WO 93/04081 or growth hormone releasing hormone (GHRH, also designated GRF) and its analogs or growth hormone and its analogs or somatomedins including IGF-1 and IGF-2 or a-adrenergic agonists such as clonidine or serotonin 5HTID agonists such as sumitriptan or agents which inhibit somatostatin or its release such as physostigmine and pyridostigmine. In particular, the compounds of this invention may be used in combination with growth hormone releasing factor, an analog of growth hormone releasing factor, IGF-1, or IGF-2. For example, a compound of the present invention may be used in combination with IGF-1 for the treatment or prevention of obesity. A still further use of the compounds of this invention is in combination with $a_2$ adrenergic agonists or $b_3$ adrenergic agonists in the treatment of obesity or in combination with parathyroid hormone in the treatment of osteoporosis. A still further use of the disclosed compounds is in combination with IGF-1 to reverse the catabolic effects of nitrogen wasting as described by Kupfer, et al, J. Clin. Invest., 91, 391(1993). In addition, a compound of this invention may be employed in conjunction with retinoic acid to improve the condition of musculature and skin that results from intrinsic aging.

The present invention is further directed to a method for the manufacture of a medicament for stimulating the release of growth hormone in humans and animals comprising combining a compound of the present invention with a pharmaceutical carrier or diluent.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses may be summarized as follows: stimulating growth hormone release in elderly humans; treating growth hormone deficient adults; prevention of catabolic side effects of glucocorticoids; treatment of osteoporosis; stimulation of the immune system, acceleration of wound healing; accelerating bone fracture repair; treatment of growth retardation; treating acute or chronic renal failure or insufficiency; treatment of physiological short stature, including growth hormone deficient children; treating short stature associated with chronic illness; treating obesity and growth retardation associated with obesity; treating growth retardation associated with Prader-Willi syndrome and Turner's syndrome; accelerating the recovery and reducing hospitalization of burn patients or following major surgery such as gastrointestinal surgery; treatment of intrauterine growth retardation, and skeletal dysplasia; treatment of hypercortisonism and Cushing's syndrome; treatment of peripheral neuropathies; replacement of growth hormone in stressed patients; treatment of osteochondrody-splasias, Noonans syndrome, sleep disorders, schizophrenia, depression, Alzheimer's disease, delayed wound healing, and psychosocial deprivation; treatment of pulmonary dysfunction and ventilator dependency; prevention or treatment of congestive heart failure, improving pulmonary function, restoring systolic and diastolic function, increasing myocardial contractility, decreasing peripheral total vascular resistance, diminishing or preventing loss of body weight and enhancing recovery following congestive heart failure; increasing appetite; attenuation of protein catabolic response after a major operation; treating malabsorption syndromes; reducing cachexia and protein loss due to chronic illness such as cancer or AIDS; accelerating weight gain and protein accretion in patients on TPN (total parenteral nutrition); treatment of hyperinsulinemia including nesidioblastosis; adjuvant treatment for ovulation induction and to prevent and treat gastric and duodenal ulcers; stimulation of thymic development and preventtion of the age-related decline of thymic function; adjunctive therapy for patients on chronic hemodialysis; treatment of immunosuppressed patients and to enhance antibody response following vaccination; increasing the total lymphocyte count of a human, in particular, increasing the $T_4/T_8$-cell ratio in a human with a depressed $T_4/T_8$-cell ratio resulting, for example, from infection, such as bacterial or viral infection, especially infection with the human immunodeficiency virus; treatment of syndromes manifested by non-restorative sleep and musculoskeletal pain, including fibromyalgia syndrome or chronic fatigue syndrome; improvement in muscle strength, mobility, maintenance of skin thickness, metabolic homeostasis, renal hemeostasis in the frail elderly; stimulation of osteoblasts, bone remodelling, and cartilage growth; prevention and treatment of congestive heart failure; protection of cardiac structure and/or cardiac function; enhancing of recovery of a mammal following congestive heart failure; enhancing and/or improving sleep quality as well as the prevention and treatment of sleep disturbances; enhancing or improving sleep quality by increasing sleep efficiency and augmenting sleep maintenance; prevention and treatment of mood disorders, in particular depression; improving mood and subjective well being in a subject suffering from depression; stimulation of the immune system in companion animals and treatment of disorders of aging in companion animals; growth promotant in livestock; and stimulation of wool growth in sheep. Further, the instant compounds are useful for increasing feed efficiency, promoting growth, increasing milk production and improving the carcass quality of livestock. Likewise, the instant compounds are useful in a method of treatment of diseases or conditions which are benefited by the anabolic effects of enhanced growth hormone levels that comprises the administration of an instant compound.

In particular, the instant compounds are useful in the prevention or treatment of a condition selected from the group consisting of: osteoporosis; catabolic illness; immune deficiency, including that in individuals with a depressed $T_4/T_8$ cell ratio; bone fracture, including hip fracture; musculoskeletal impairment in the elderly; growth hormone deficiency in adults or in children; short stature in children; obesity; sleep disorders; cachexia and protein loss due to chronic illness such as AIDS or cancer; and treating patients recovering from major surgery, wounds or burns, in a patient in need thereof.

In addition, the instant compounds may be useful in the treatment of illnesses induced or facilitated by corticotropin releasing factor or stress- and anxiety-related disorders, including stress-induced depression and headache, abdominal bowel syndrome, immune suppression, HIV infections, Alzheimer's disease, gastrointestinal disease, anorexia nervosa, hemorrhagic stress, drug and alcohol withdrawal symptoms, drug addiction, and fertility problems.

It will be known to those skilled on the art that there are numerous compounds now being used in an effort to treat the diseases or therapeutic indications enumerated above. Combinations of these therapeutic agents some of which have also been mentioned above with the growth hormone secretagogues of this invention will bring additional, complementary, and often synergistic properties to enhance the growth promotant, anabolic and desirable properties of these various therapeutic agents. In these combinations, the therapeutic agents and the growth hormone secretagogues of this invention may be independently present in dose ranges from one one-hundredth to one times the dose levels which are effective when these compounds and secretagogues are used singly.

Combined therapy to inhibit bone resorption, prevent osteoporosis and enhance the healing of bone fractures can be illustrated by combinations of bisphosphonates and the growth hormone secretagogues of this invention. The use of bisphosphonates for these utilities has been reviewed, for example, by Hamdy, N.A.T. Role of Bisphosphonates in Metabolic Bone Diseases. Trends in Endocrinol. Metab.,, 4, 19–25 (1993). Bisphosphonates with these utilities include alendronate, tiludronate, dimethyl—APD, risedronate, etidronate, YM-175, clodronate, pamidronate, and BM-210995. According to their potency, oral daily dosage levels of the bisphosphonate of between 0.1 mg and 5 g and daily dosage levels of the growth hormone secretagogues of this invention of between 0.01 mg/kg to 20 mg/kg of body weight are administered to patients to obtain effective treatment of osteoporosis.

Osteoporosis and other bone disorders may also be treated with compounds of this invention in combination with calcitonin, estrogens, raloxifene and calcium supplements such as calcium citrate or calcium carbonate.

In the case of alendronate daily oral dosage levels of 0.1 mg to 50 mg are combined for effective osteoporosis therapy with 0.01 mg/kg to 20 mg/kg of the growth hormone secretagogues of this invention.

Anabolic effects especially in the treatment of geriatric male patients are obtained with compounds of this invention in combination with anabolic steroids such as oxymetholone, methyltesterone, fluoxymesterone and stanozolol.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, and elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 10 mg/kg. of body weight daily are administered to patients and animals, e.g., mammals, to obtain effective release of growth hormone. Preferably, the dosage level will be about 0.001 to about 25 mg/kg per day; more preferably about 0.01 to about 10 mg/kg per day.

The following examples are provided for the purpose of further illustration only and are not intended to be limitations on the disclosed invention.

EXAMPLE 1

2-Amino-2-methyl-N-[3(R)-2,3,4,5-tetrahydro-5-[[2'-[[[(methylamino)-carbonyl]amino]methyl][1,1'-biphenyl]-4-yl]methyl]-4-oxo-1H-naphtho[2,1-b]azepin-3(R)-yl]propanamide, hydrochloride Step A: 2-Benzyloxycarbonylamino-2-methyl-N-[2,3,4,5-tetrahydro-4-oxo-1H-naphtho[2,1-b]azepin-3(R)-yl] propanamide A solution of 3(R)amino-2,3,4,5-tetrahydro-5H-1-naphtho[2,1-b]azepine (Eur. Pat. Appl. WO 96/05195) in methylene chloride is treated with N-carbobenzyloxy-2-methylalanine (1 eq.) and triethylamine (2 eq.). The reaction flask is immersed in an ambient temperature water bath then benzotriazol-1-yloxytris(dimethylamino)phosphonium hexafluorophosphate (1.2 eq) is added all at once and the mixture stirred at room temperature for 2 hours. The reaction mixture is added to ethyl acetate and is washed three times with 5% aqueous citric acid, twice with saturated aqueous sodium bicarbonate and once with saturated aqueous sodium chloride. The organic layer is removed, dried over magnesium sulfate, filtered and the filtrate is concentrated under vacuum. The residue is purified by chromatography on silica, eluting with ethyl acetate/hexane the product.

Step B: 4-Bromobenzyl-t-butyldiphenylsilyl ether

To a solution of 28.2 g (0.150 mol) of 4-bromobenzylalcohol in 470 mL of dry dimethylformamide under nitrogen atmosphere was added 31.4 mL (0.225 mol) of triethylamine. The reaction mixture was cooled to 0° C. and 43 mL (0.17 mol) of t-butylchlorodiphenylsilane was added dropwise by addition funnel. The reaction mixture was stirred at ambient temperature overnight then poured into a separatory funnel containing 1 L of diethyl ether and 500 mL of water. To this mixture was added 125 mL of 2N aqueous hydrochloric acid. The layers were separated and the aqueous layer was extracted with diethyl ether (2×350 mL). The organic extracts were combined, washed with water (2×250 mL) and dried over magnesium sulfate. The solids were removed by filtration and the solvent removed under vacuum to give an oil which crystallized on standing. The flask containing the crude product was placed in the freezer overnight then triturated with a minimal amount of methanol and filtered. The solid was air dried for several hours then dried under vacuum overnight to afford 59.5 g (93%) of product as an off-white solid (mp 44–47° C.). $^1$H NMR (200 MHz, CDCl$_3$): d 1.15 (s, 9 H), 4.76 (s, 2 H), 7.25 (d, 8 Hz, 2 H), 7.45 (m, 8 H), 7.75 (m, 4 H). FAB-MS: calculated for C$_{23}$H$_{25}$BrOSi 424; found 425 (M+H, 7%).

Step C: 4-(t-Butyldiphenylsilyoxymethyl)phenylboronic acid

To a solution of 20 g (47 mmol) of 4-bromobenzyl-t-butyldiphenyl silyl ether (Step B) in 200 mL of dry tetrahydrofuran under a nitrogen atmosphere at −78° C. was added dropwise by syringe 19.74 mL (49.35 mmol) of a 2.5M solution of n-butyl lithium in hexanes over twenty minutes. The resulting mixture was stirred for thirty minutes, then 11.6 mL (50.3 mmol) of triisopropyl borate was added by syringe. The reaction mixture was stirred at −78° C. for thirty minutes then slowly warmed to room temperature and stirred for an additional two hours. The reaction mixture was then quenched by the addition of 750 mL of water containing 100 mL of concentrated hydrochloric acid and 500 mL of diethyl ether. The mixture was stirred for one hour and then the organic layer was separated. The aqueous layer was extracted with diethyl ether (2×400 mL). The combined ether extracts were washed with saturated aqueous sodium chloride (4×100 mL), dried over magnesium sulfate and filtered. The solvent was removed under vacuum to give an oil which was crystallized by dissolving in hexanes and evaporation of the solvent under vacuum to afford 15.6 g (85%) of product as a white solid (mp 171–174° C.). $^1$H NMR (200 MHz, CDCl$_3$): d 1.11 (s, 9 H), 4.86 (s, 2 H), 7.40 (m, 6 H), 7.58 (d, 8 Hz, 2 H), 7.70 (m, 4 H), 8.22 (d, 8 Hz, 2 H). FAB-MS: calculated for C$_{23}$H$_{27}$BrO$_3$Si 390; found 372 (M-H$_2$O).

Step D: N-(t-Butoxycarbonyl)-2-bromobenzylamine

To a slurry of 8.88 g (39.9 mmol) of 2-bromobenzylamine hydrochloride in 100 mL of dry methylene chloride under a nitrogen atmosphere was added by syringe 12.24 mL (87.80 mmol) of triethylamine. The resulting solution was stirred at 0° C. for five minutes then treated with 9.6 g (44 mmol) of di-t-butyldicarbonate. The reaction was stirred at room temperature for two hours then diluted with 350 mL of methylene chloride. The solution was washed with water (2×150 mL), saturated aqueous ammonium chloride (150 mL), saturated aqueous sodium bicarbonate (4×150 mL) and saturated aqueous sodium chloride (150 mL), dried over sodium sulfate and filtered. The solvent was removed under vacuum to give an oil which was crystallized by dissolving in hot hexanes, filtering and cooling the solution. The product was filtered and dried under vacuum to afford 8.66 g (90%) of the product as a white solid (mp 51–53° C.). $^1$H NMR (200 MHz, CDCl$_3$): d 1.41 (s, 9 H), 4.37 (d, 5 Hz, 2 H), 5.00 (s, 1 H), 7.10 (m, 1 H), 7.25 (m, 1 H), 7.35 (m, 1 H), 7.40 (d, 6 Hz, 1 H). FAB-MS: calculated for C$_{12}$H$_{16}$BrNO$_2$ 285; found 286 (M+H).

Step E: 2'-[(t-Butoxycarbonylamino)methyl]4-[(t-butyldiphenylsiloxy)methyl]-1,1'-biphenyl To a solution of 3.2 g (8.2 mmol) of 4-(t-butyldiphenylsilyoxymethyl)phenylboronic acid (Step C) in 64 mL of benzene was added 2.2 mL of water, 6.4 mL of 5N aqueous sodium hydroxide, and 8.3 mL of isopropanol. To this mixture was added 180 mg (0.16 mmol) of tetrakis (triphenylphosphine) palladium and 2.20 g (7.81 mmol) of N-(t-butoxycarbonyl)-2-bromobenzylamine (Step D). The resulting mixture was heated under nitrogen at reflux for 2 hours then cooled to room temperature. The reaction mixture was diluted with 100 mL of water, transferred to a separators funnel and extracted with ether (3×150 mL). The combined ether extracts were washed with saturated aqueous sodium bicarbonate (100 mL) and saturated aqueous sodium chloride (100 mL), dried over magnesium sulfate and filtered. The solvent was removed under vacuum to give a crude product which was purified by column chromatography on silica gel eluting with hexaneslethyl acetate (9:1) to afford 4.31 g (100%) of the product as a clear oil. $^1$H NMR (200 MHz, CDCl$_3$): d 1.11 (s, 9 H), 1.41 (s, 9 H), 4.27 (d, 6 Hz, 2 H), 4.45 (m, 1 H), 4.81 (s, 2 H), 7.20–7.49 (m, 14 H), 8.72 (m, 4 H). FAB-MS: calculated for $C_{35}H_{41}NO_3Si$ 551; found 552 (M+H).

Step F: 2'-[(t-Butoxycarbonylamino)methyl]-1,1'-biphenyl-4-methanol

To a solution of 3.85 g (7.00 mmol) of 2'-[(t-butoxycarbonylamino)methyl]-4-[(t-butyldiphenylsiloxy) methyl -1,1'-biphenyl (Step E) in 25 mL of dry tetrahydrofuran under a nitrogen atmosphere was added by syringe 10.5 mL (0.530 mmol) of a 1.0M solution of tetra-n-butylammonium fluoride in tetrahydrofuran. The reaction mixture was stirred for two hours then diluted with 700 mL of diethyl ether. The mixture was washed with water (3×150 mL), saturated aqueous sodium bicarbonate (50 mL), saturated aqueous sodium chloride (50 mL), then dried over magnesium sulfate and filtered. The solvent was removed under vacuum to give an oil which was purified by column chromatography on silica gel eluting with hexanes/ethyl acetate (55:45) to afford 2.02 g (92%) of the product as a white solid (mp 89–93° C.). $^1$H NMR (200 MHz, CDCl$_3$): d 1.40 (s, 9 H), 2.50 (s, 2 H), 4.20 (s, 2 H), 4.70 (s, 2 H), 7.18–7.45 (m, 8 H). FAB-MS: calculated for $C_{19}H_{23}NO_3$ 313; found 314 (M+H).

Step G: 2'-[(t-Butoxycarbonylamino)methyl]-1,1'-biphenyl-4-methanol, methanesulfonate ester To solution of 53 mg (0.17 mmol) of 2'-[(t-butoxycarbonylamino)methyl]-1,1'-biphenyl-4-methanol (Step E) in 1 mL of dry methylene chloride under nitrogen atmosphere at 0° C. was added by syringe 0.035 mL (0.25 mmol) of triethylamine followed by 0.016 mL (0.20mmol) of methanesulfonyl chloride. The reaction mixture was stirred for 2 hours at 0° C. then diluted with 75 mL of methylene chloride, washed with water, saturated aqueous sodium bicarbonate, saturated aqueous sodium chloride, dried over sodium sulfate and filtered. The solvent was removed under vacuum to give 61 mg (97%) of the product as a white solid which was used in the next step without further purification. $^1$H NMR (200 MHz, CDCl$_3$): d 1.38 (s, 9 H), 2.95 (s, 3 H), 4.20 (d, 5 Hz, 2 H), 4.65 (s, 1 H), 5.25 (s, 2 H), 7.18–7.50 (m, 8 H). FAB-MS: calculated for $C_2OH_{25}NO_5S$ 391; found 392 (M+H).

Step H: 2-Benzyloxycarbonylamino-2-methyl-N-[2,3,4,5-tetra-hydro-4-oxo-1-[[2'-[(t-butoxycarbonylamino)methyl]-[1,1'-biphenyl]-4-yl]methyl]-1H-naphtho[2,1-b]azepin-3(R)-yl]-propanamide To a solution of 2-benzyloxycarbonylamino-2-methyl-N-[2,3,4,5-tetrahydro-4-oxo-1H-naphtho[2,1-b]azepin-3(R)-yl]prop-anamide (Step A) in dry dimethylformamide under nitrogen at 0° C. is added of 60% sodium hydride/oil dispersion (1.05 eq.). After stirring for 15 minutes, a solution of 2'-[(t-butoxycarbonylamino)methyl]-1,1'-biphenyl-4-methanol, methanesulfonate ester (Step F) in dimethylformamide is added by cannula. The flask which originally contained the methanesulfonate ester is rinsed with dimethylformamide which is added to the reaction mixture. After stirring at 0° C. for 15 minutes, the reaction mixture is diluted with ethyl acetate and 50% saturated ammonium chloride. The mixture is transferred to a separatory funnel and the aqueous layer is separated. The organic layer is washed with 100 mL of saturated aqueous sodium bicarbonate and saturated aqueous sodium chloride. The organic layer is dried over magnesium sulfate, filtered and the solvent removed under vacuum. The residue is purified by flash chromatography on silica gel eluting with ethyl acetate/hexane to afford the product.

Step I: 2-Benzyloxycarbonylamino-2-methyl-N-[2,3,4,5-tetrahydro-4-oxo-1-[[2'-(aminomethyl)[1,1'-biphenyl]-4-yl]methyl]-1H-naphtho[2,1-b]azepin-3(R)-yl] propanamide, hydrochloride To a solution of of 2-benzyloxycarbonylamino-2-methyl-N-[2,3,4,5-tetrahydro-4-oxo-1-[[2'-[(t-butoxycarbonylamino)methyl][1,1'-biphenyl]-4-yl]methyl]-1H-naphtho[2,1-b]azepin-3(R)-yl]propanamide (Step H) in methanol is added 9N aqueous hydrochloric acid. The reaction mixture is stirred overnight at room temperature then the solvent is removed under vacuum. The resulting oil is dissolved in methanol and the solvent is removed under vacuum to afford the title compound.

Step J: 2-Benzyloxycarbonylamino-2-methyl-N-[3(R)-2,3,4,5-tetrahydro-5-[[2'-[[[(methylamino)carbonyl]amino] methyl]-[1,1'-biphenyl]-4-yl]methyl]-4-oxo-1H-naphtho [2,1-b]azepin-3(R)-yl]propanamide To a solution of 2-benzyloxycarbonylamino-2-methyl-N-[2,3,4,5-tetrahydro-4-oxo-1-[[2'-(aminomethyl)[1,1'-biphenyl]-4-yl]methyl]-1H-naphtho[2,1-b]azepin-3(R)-yl] propanamide, hydrochloride (Step I) in dry methylene chloride under nitrogen atmosphere is added (3 eq.) of triethylamine followed by methyl isocyanate (1.1 eq). After stirring at room temperature the solvent is removed under vacuum. The resulting material is purified by flash column chromatography on silica gel eluting with ethyl acetate/methanol to afford the product.

Step K: 2-Amino-2-methyl-N-[3(R)-2,3,4,5-tetrahydro-5-[[2'-[[[(methylamino)carbonyl]amino]methyl][1,1'-biphenyl]-4-yl]methyl]-4oxo-1H-naphtho[2,1-b]azepin-3(R)-yl]propanamide To a solution 2-benzyloxycarbonylamino-2-methyl-N-[3(R)-2,3,4,5-tetrahydro-5-[[2'-[[[(methyl-amino)carbonyl] amino]methyl][1,1'-biphenyl]-4-yl]methyl]-4-oxo-1H-naphtho[2,1-b]azepin-3(R)-yl]propanamide (Step J) in dry methanol is added 0.1 equiv. by weight of palladium hydroxide. The mixture is stirred under hydrogen atmosphere. The mixture is filtered through Celite. The filter pad is washed with 50 mL of methanol. The filtrate is combined and the solvent is removed under vacuum. The residue is purified by reverse phase chromatography to afford the title compound.

EXAMPLE 2

3-Amino-3-methyl-N-[3(R)-2,3,4,5-tetrahydro-5-[[2'-[[[(methylamino)carbonyl]amino]methyl][1,1'-biphenyl]-4-yl]methyl]-4-oxo-1H-naphtho[2,1-b] azepin-3(R)-yl]butanamide Step A: 3-Benzyloxycarbonylamino-3-methyl-N-[2,3,4,5-tetrahydro-4-oxo-1H-1-naphtho[2,1-b]azepin-3(R)-yl]-butanamide Product of step A is prepared from 3-benzyloxycarbonylamino-3-methylbutanoic acid and 3(R)-amino-3(R)-2,3,4,5-tetrahydro-5H-naphtho[2,1-b] azepin-4-one (Eur. Pat. Appl. WO 96/05195) according to the procedure described in Example 1, Step A.

Step B: 3-Benzyloxycarbonylamino-3-methyl-N-[2,3,4,5-tetra-hydro-4-oxo-5-[[2'-[(t-butoxycarbonylamino)methyl]-[1,1'-biphenyl]-4-yl]methyl]-1H-naphtho[2,1-b]azepin-3(R)-yl]-butanamide The product of Step B is prepared from 3-benzyloxycarbonylamino-3-methyl-N-[2,3,4,5-tetrahydro-4-oxo-1H-naphtho[2,1-b]azepin-3(R)-yl]butanamide (Step A) and 2'-[(t-butoxycarbonylamino)methyl]-1,1'-biphenyl-4-methanol, methanesulfonate ester (Example 1, Step G) according to the procedure for Example 1, Step H.

Step C: 3-Benzyloxycarbonylamino-3-methyl-N-[2,3,4,5-tetrahydro-4-oxo-5-[[2'-(aminomethyl)[1,1'-biphenyl]-4-yl]methyl]-1H-naphtho[2,1-b]azepin-3(R)-yl]butanamide, hydrochloride The product of Step C is prepared from 3-benzyloxycarbonylamino-3-methyl-N-[2,3,4,5-tetrahydro-4-oxo-5-[[2'-[(t-butoxylcarbonylamino)methyl]-[1,1'-biphenyl]-4-yl]methyl]1H-naphtho[2,1-b]azepin-3(R)-yl]-butanamide (Step B) according to the procedure for Example 1, Step I.

Step D: 3-Benzyloxycarbonylamino-3-methyl-N-[3(R)-2,3,4,5-tetrahydro-5-[[2'-[[[(methylamino)carbonyl]amino]methyl]-[1,1'-biphenyl]-4-yl]methyl]-4-oxo-1H-naphtho[2,1-b]azepin-3(R)-yl]butanamide The title compound is prepared from 3-benzyloxycarbonylamino-3-methyl-N-[2,3,4,5-tetrahydro-4-oxo-5-[[2'-(aminomethyl)[1,1'-biphenyl]-4-yl]methyl]-1H-naphtho[2,1-b]azepin-3(R)-yl]butanamide, hydrochloride (Step C) according to the procedure for Example 1, Step J.

Step E: 3-Amino-3-methyl-N-[3(R)-2,3,4,5-tetrahydro-5-[[2'-[[[(methylamino)carbonyl]amino]methyl][1,1'-biphenyl]-4-yl]methyl]-4-oxo-1H-naphtho[2,1-b]azepin-3(R)-yl]butanamide The title compound is prepared from 3-benzyloxycarbonylamino-3-methyl-N-[3(R)-2,3,4,5-tetrahydro-5-[[2'-[[[(methylamino)carbonyl]amino]methyl][1,1'-biphenyl]-4-yl]methyl]-4-oxo-1H-naphtho[2,1-b]azepin-3(R)-yl]butanamide (Step D) according to the procedure for Example 1, Step K

EXAMPLE 3

N-[5-[[2'-[(Methylaminocarbonyl)amino][1,1'-biphenyl]4-yl]methyl]-2,3,4,5-tetrahydro-4-oxo-1H-naphtho[2,1b]azepin-3(R)-yl]-3-[2(R)-hydroxypropyl]amino-3-methylbutanamide, trifluoroacetate Step A: N-[5-[[2'-[(Methylaminocarbonyl)amino][1,1'-biphenyl]-4-yl]methyl]-2,3,4,5-tetrahydro-4-oxo-1H-naphtho[2,1b]azepin-3(R)-yl]-3-[2(R)-benzyloxypropyl]amino-3-methylbutanamide, trifluoroacetate To a solution of 3-amino-3-methyl-N-[3(R)-2,3,4,5-tetrahydro-5-[[2'-[[[(methylamino)-carbonyl]amino]methyl][1,1'-biphenyl]-4-yl]methyl]-4-oxo-1H-naphtho[2,1-b]azepin-3(R)-yl]butanamide (Example 3) in methanol is added powdered 4 molecular sieves and (R)-2-benzyloxypropanal (5 equiv.) (prepared from ethyl D-lactate according to the procedure of Hanessian and Kloss, Tetrahedron Lett., 26, 1261–1264 (1985).) in dry methanol. After adjusting the pH of the suspension to 5.5 with glacial acetic acid and sodium acetate the reaction mixture is stirred at room temperature several hours. Dropwise, a solution of 1.0M sodium cyanoborohydride in tetrahydrofuiran (5 equiv) is added and the reaction mixture stirred at room temperature. The reaction mixture is filtered and the filtrate is treated with of trifluoroacetic acid (CAUTION! evolution of hydrogen cyanide). After stirring for 10 minutes, all volatiles are removed under vacuum and the residue is chromatographed on silica gel, eluting with methylene chloride/methanol/concentrated ammonium hydroxide to yield product.

Step B: N-[1-[[2'-[(Methylaminocarbonyl)amino][1,1'-biphenyl]-4-yl]methyl]-2,3,4,5-tetrahydro-4-oxo-1H-naphtho[2,1b]azepin-3(R)-yl3-3-[2(R)-hydroxypropyl]amino-3-methylbutanamide, trifluoroacetate A solution of the intermediate obtained in Step A in 5 mL of methanol containing trifluoroacetic acid is hydrogenated at ambient temperature and 40 psi for 24 hours over 30% palladium on carbon(10% by weight). The reaction mixture is filtered through Celite and the filtrate is evaporated under vacuum and the residue is purified by reverse phase medium pressure liquid chromatography on C8, eluting with methanol/0.1% aqueous trifluoroacetic acid to the title compound.

EXAMPLE 4

N-[1-[[2'-[(Methylaminocarbonyl)amino][1,1'-biphenyl]-4-yl]methyl]-2,3,4,5-tetrahydro-4-oxo-1H-naphtho-2,1b]azepin-3(R)-yl]-3-[2(S),3-dihydroxypropyl]amino-3-methylbutanamide, trifluoroacetate To a stirred solution of 3-Amino-3-methyl-N-[3(R)-2,3,4,5-tetrahydro-5-[(2'-[[[(methylamino)-carbonyl]amino]methyl][1,1'-biphenyl]-4-yl]methyl]-4-oxo-1H-naphtho[2,1-b]azepin-3(R)-yl]butanamide (Example 2) in dry methanol under nitrogen is added powdered 4A molecular sieves followed by a solution of D-glyceraldehyde acetonide (6 equiv.) used crude as prepared according to the procedure of L. W. Hertel, C. S. Grossman and J. S. Kroin, Synth. Comm., 21, 151–154 (1991).) in dry methanol. The pH of the mixture was carefully adjusted to 5.5 with glacial acetic acid and sodium acetate. The reaction was stirred at room temperature for 2 hours at which time a 1.0M solution of sodium cyanoborohydride in tetrahydrofuran is added dropwise by syringe. The reaction mixture is stirred at room temperature for 18 hours, then filtered and the filtrate treated with trifluoroacetic acid and water. After 1 hour, the reaction mixture is evaporated under vacuum and the residue purified by reverse phase medium pressure liquid chromatography on C8, eluting with methanol/0.1% aqueous trifluoroacetic acid to give the title compound.

EXAMPLE 5

2-Amino-2-methyl-N-[2,3,4,5-tetrahydro-5-[[2'-[[[(methylamino)carbonyl]amino]methyl][1,1'-biphenyl]-4-yl]methyl]-4-oxonaphtho[2,1-b]thiazepin-3(S)-yl]propanamide, trifluoroacetate Step A: 2-Benzyloxycarbonylamino-2-methyl-N-[3(S)-2,3,4,5-tetrahydro-4-oxo-5H-1,5-naphtho[2,1-b]thiazepin-3(S)-yl]propanamide The product of step A is prepared from 3(S)-amino-3(S)-2,3,4,5-tetrahydro-1,5-naphtho[2,1-b]thiazepin-4(5H)-one (prepared from D-cysteine (S-cysteine) and 2-fluoro-1-nitronaphthalene (Bull. Soc. Chim. Belges. 75 (9–10), p577–581 (1966)) by the method of Slade, et al, J. Med. Chem., 28, 1517–1521(1985) and N-benzyloxycarbonyl-2-methylalanine by the procedure described in Example 1, Step I.

Step B: 2'-[(t-Butoxycarbonylamino)methyl]-1,1'-biphenyl-4-methanol, acetate ester To solution of 500 mg (1.60 mmol) of 2'-[(t-butoxycarbonylamino)methyl]-1,1'-biphenyl-4-methanol (Example 1, Step F) in 1 mL of dry methylene chloride under a nitrogen atmosphere at room temperature was added by syringe 0.267 mL (1.91 mmol) of triethylamine followed by 0.165 mL (1.76 mmol) of acetic anhydride. The reaction mixture was stirred for 1 hour then diluted with 150 mL of ethyl acetate, washed with saturated aqueous ammonium chloride, saturated aqueous sodium bicarbonate, saturated aqueous sodium chloride, dried over magnesium sulfate and filtered. The solvent was removed under vacuum to give 583 mg (>100%, containing a minor amount of ethyl acetate) of the product as a white solid which was used in the next step without further purification. $^1$H NMR (200 MHz, CDCl$_3$): d 1.39 (s, 9 H), 2.10 (s, 3 H), 4.22 (d, 6 Hz, 2 H), 4.65 (s, 1 H), 5.12 (s, 2 H), 7.18–7.48 (m, 8 H). FAB-MS: calculated for $C_{21}H_{25}NO_4$ 355; found 356 (M+H).

Step C: 2'-Aminomethyl-1,1'-biphenyl-4-methanol, acetate ester, trifluoroacetate Prepared from 2'-[(t-butoxycarbonylamino)methyl]-1,1'-biphenyl-4-methanol, acetate ester (Step B) by treatment with trifluoroacetic acid in methylene chloride (1:1) and removal of the solvent under vacuum. $^1$H NMR (200 MHz, CDCl$_3$): d 2.03 (s, 3 H), 3.98 (s, 2 H), 5.07 (s, 2 H), 7.18–7.48 (m, 8 H), 7.75 (s, 3 H). FAB-MS: calculated for $C_{16}H_{17}NO_2$ 255; found 256 (M+H, 80%).

Step D: 2'-[[(Methylamino)carbonyl]amino]methyl-1,1'-biphenyl-4-methanol, acetate ester Prepared from 2'-aminomethyl-1,1'-biphenyl-4-methanol, acetate ester, trifluoroacetate (Step C) according to the procedure described in Example 1, Step J. $^1$H NMR (200 MHz, CDCl$_3$): d 2.10 (s, 3 H), 2.65 (d, 4.8 Hz, 3 H), 4.27 (d, 4.8 Hz, 2 H), 4.52 (m, 1 H), 5.12 (s, 2 H), 7.18–7.48 (m, 8 H). FAB-MS: calculated for $C_{18}H_{20}N_2O_3$ 312; found 313 (M+H, 100%).

Step E: 2'-[[(Methylamino)carbonyl]amino]methyl-1,1'-biphenyl-4-methanol

To a solution of 498 mg (1.60 mmol) of 2'-[[(methylamino)carbonyl]amino]methyl-1,1'-biphenyl-4-methanol, acetate ester (Step D) in 10 mL of THF/water (3:1) was added 335 mg (7.98 mmol) of lithium hydroxide monohydrate. After stirring at room temperature for 16 hours the reaction mixture was diluted with 150 mL of ethyl acetate and washed with brine (3×50 mL). The organic layer was dried over magnesium sulfate, filtered and the solvent removed under vacuum to afford 411 mg (95%) of the product as a white solid. $^1$H NMR (200 MHz, CD$_3$OD): d 2.64 (s, 3 H), 4.20 (s, 2 H), 4.62 (s, 2 H), 7.12–7.45 (m, 8 H). FAB-MS: calculated for $C_{16}H_{18}N_2O_2$ 270; found 271 (M+H, 100%).

Step F: 2'-[[(Methylamino)carbonyl]amino]methyl-1,1'-biphenyl-4-methanol, methanesulfonate ester To solution of 100 mg (0.17 mmol) of 2'-[[(methylamino)carbonyl]amino]methyl-1,1'-biphenyl-4-methanol (Step E) in 5 mL of dry methylene chloride and 1 mL dry dimethylformamide under a nitrogen atmosphere at 0° C. was added by syringe 0.077 mL (0.56 mmol) of triethylamine followed by 0.034 mL (0.44 mmol) of methanesulfonyl chloride. The reaction mixture was stirred for 30 minutes at 0° C. then diluted with 75 mL of methylene chloride, washed with water, saturated aqueous sodium bicarbonate, saturated aqueous sodium chloride then dried over sodium sulfate and filtered. The solvent was removed under vacuum to give 128 mg (100%) of the product as a white solid which was used in the next step without further purification. $^1$H NMR (200 MHz, CDCl$_3$): d 2.66 (d, 4 Hz, 3 H), 2.97 (s, 3 H), 4.26 (d, 5 Hz, 2 H), 4.42 (m, 1 H), 5.26 (s, 2 H), 7.18–7.48 (m, 8 H). FAB-MS: calculated for $C_{17}H_{20}N_2O_4S$ 348; found 349 (M+H, 100%).

Step G: 2-Benzyloxycarbonylamino-2-methyl-N-[3(S)-2,3,4,5-tetrahydro-5-[[2'-[[[(methylamino)carbonyl]amino]methyl][1,1'-biphenyl]-4-yl]methyl]-4-oxonaphtho[2,1-b]thiazepin-3(S)-yl]propanamide The product of step G is prepared from 2-benzyloxycarbonylamino-2-methyl-N-[3(S)-2,3,4,5tetrahydro-4-oxo-5H-1,5-naphtho[2,1-b]thiazepin-3(S)-yl]propanamide (Step A) and 2'-[[(methylamino)carbonyl]amino]methyl-1,1'-biphenyl-4-methanol, methanesulfonate ester (Step F) according to the procedure described in Example 1, Step H.

Step H: 2-Amino-2-methyl-N-[3(S)-2,3,4,5-tetrahydro-5-[[2'-[[[(methylamino)carbonyl]amino]methyl][1,1'-biphenyl]-4-yl]methyl]-4-oxonaphtho[2,1-b]thiazepin-3(S)-yl]propanamide The title compound is prepared from 2-benzyloxycarbonylamino-2-methyl-N-[3(S)-2,3,4,5-tetrahydro-5-[[2'-[[[(methylamino)carbonyl]amino]methyl][1,1'-biphenyl]-4-yl]methyl]-4-oxonaphtho[2,1-b]thiazepin-3(S)-yl]propanamide (Step G) by treatment with HBr in acetic acid followed by purification by reverse phase mplc eluting with methanol/01% aq. TFA.

EXAMPLE 6

2-Amino-2-methyl-N-[2,3,4,5-tetrahydro-5-[[2'-[[[(methylamino)carbonyl]amino]methyl][1,1'-biphenyl]-4-yl]methyl]-4-oxonaphtho[2,1-b]oxazepin-3(S)-yl]propanamide, trifluoroacetate The title compound is prepared from 3(S)-amino-3(S)-2,3,4,5-tetrahydro-1,5-naphtho[2,1-b]oxazepin-4(5H)-one (prepared from D-serine and 2-fluoro-1-nitronaphthalene (Bull. Soc. Chim. Belges. 75 (9–10), p577–581 (1966)) by the method of Slade, et al, J. Med. Chem., 28, 1517–1521 (1985); N-benzyloxycarbonyl-2-methylalanine; and 2'-[[(methylamino)carbonyl]amino]methyl-1,1'-biphenyl-4-methanol, methanesulfonate ester (Example 5, Step F) by the procedure described in Example 5, Steps A–H.

EXAMPLE 7

Utilizing the procedures described in Examples 1 to 6 and general methods of organic synthesis described in the chemical literature and familiar to one skilled in the art, the following compounds of Formula 1 can be prepared from the appropriately substituted starting materials and reagents.

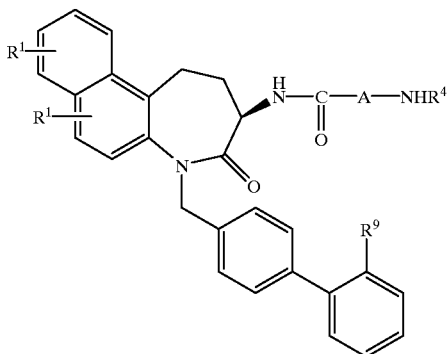
| R¹ | R⁹ | A | R⁴ |
|---|---|---|---|
| H | 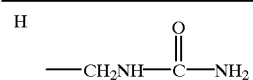 | 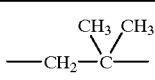 | 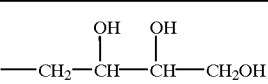 |
| H | 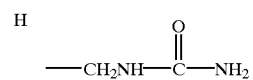 |  | —CH₂CH₂OH |
| H | 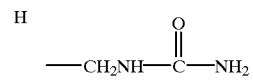 | 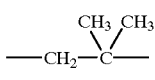 | 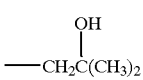 |
| H | 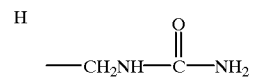 | 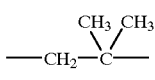 | 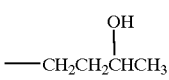 |
| H | 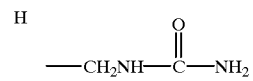 | 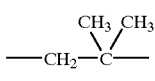 | 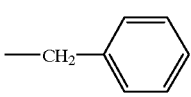 |
| H |  | 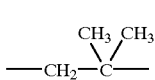 | —CH₂CH₂CH₃ |
| H | 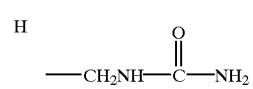 | 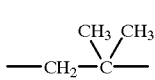 | —CH₃ |
| H | 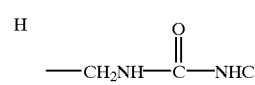 | 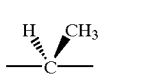 | H |
| H | 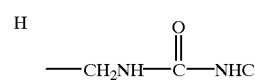 | 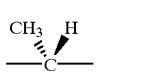 | H |
| H | 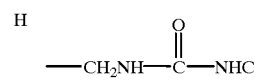 | 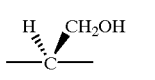 | H |
| H | 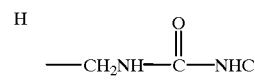 | 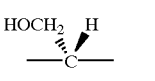 | H |
| H | (CH₂NH—C(O)—NHCH₃) | (CH₃, CH₂OH) | H |

-continued

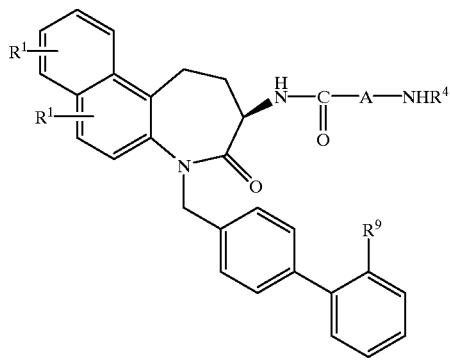

| R¹ | R⁹ | A | R⁴ |
|---|---|---|---|
| H | —CH₂NH—C(O)—NHCH₃ | —CH₂—C(CH₃)(CH₂OH)— | H |
| H | —CH₂NH—C(O)—NHCH₃ | —CH₂—C(HOCH₂)(CH₃)— | H |
| H | —CH₂NH—C(O)—NHCH₂CH₃ | —C(H)(CH₃)— | —CH₂—CH(OH)—CH₃ |
| H | —CH₂NH—C(O)—NHCH₂CH₃ | —C(CH₃)(H)— | —CH₂—CH(OH)—CH₃ |
| H | —CH₂NH—C(O)—NHCH₂CH₃ | —C(H)(CH₂OH)— | —CH₂—CH(OH)—CH₃ |
| H | —CH₂NH—C(O)—NHCH₂CH₃ | —C(HOCH₂)(H)— | —CH₂—CH(OH)—CH₃ |
| H | —CH₂NH—C(O)—NHCH₂CH₃ | —C(CH₃)(CH₂OH)— | —CH₂—CH(OH)—CH₃ |
| H | —CH₂NH—C(O)—NHCH₂CH₃ | —CH₂—C(CH₃)(CH₂OH)— | —CH₂—CH(OH)—CH₃ |
| H | —CH₂NH—C(O)—NHCH₂CH₃ | —CH₂—C(HOCH₂)(CH₃)— | —CH₂—CH(OH)—CH₃ |
| H | —CH₂NH—C(O)—NHCH₂Ph | —C(H)(CH₃)— | —CH₂—CH(OH)—CH₂OH |
| H | —CH₂NH—C(O)—NHCH₂Ph | —C(CH₃)(H)— | —CH₂—CH(OH)—CH₂OH |
| H | —CH₂NH—C(O)—NHCH₂Ph | —C(H)(CH₂OH)— | —CH₂—CH(OH)—CH₂OH |

-continued

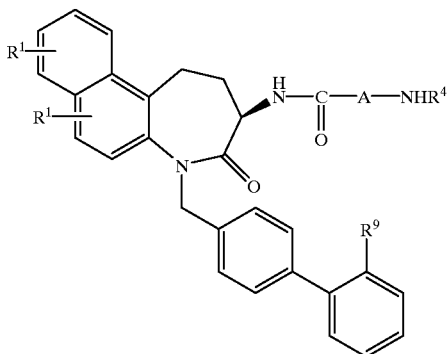

| R¹ | R⁹ | A | R⁴ |
|---|---|---|---|
| H | —CH₂NH—C(=O)—NHCH₂Ph | HOCH₂, H on C (wedge) | —CH₂—CH(OH)—CH₂OH |
| H | —CH₂NH—C(=O)—NHCH₂Ph | CH₃, CH₂OH on C (wedge) | —CH₂—CH(OH)—CH₂OH |
| H | —CH₂NH—C(=O)—NHCH₂Ph | —CH₂—C(CH₃)(CH₂OH) | —CH₂—CH(OH)—CH₂OH |
| H | —CH₂NH—C(=O)—NHCH₂Ph | —CH₂—C(HOCH₂)(CH₃) | —CH₂—CH(OH)—CH₂OH |
| H | —CH₂NH—C(=O)—N(CH₃)₂ | —CH₂—C(CH₃)(CH₃)— | H |
| H | —CH₂NH—C(=O)—NHCH(CH₃)₂ | —CH₂—C(CH₃)(CH₃)— | H |
| H | —CH₂N(CH₃)—C(=O)—NHCH₃ | —CH₂—C(CH₃)(CH₃)— | H |
| H | —CH₂NH—C(=O)—NHCH₂Ph | —CH₂—C(CH₃)(CH₃)— | H |
| H | —CH₂NH—C(=O)-pyrrolidinyl | —CH₂—C(CH₃)(CH₃)— | H |
| H | —CH₂NH—C(=O)-morpholinyl | —CH₂—C(CH₃)(CH₃)— | H |
| H | —CH₂NH—C(=O)-piperazinyl(NH) | —CH₂—C(CH₃)(CH₃)— | H |

-continued

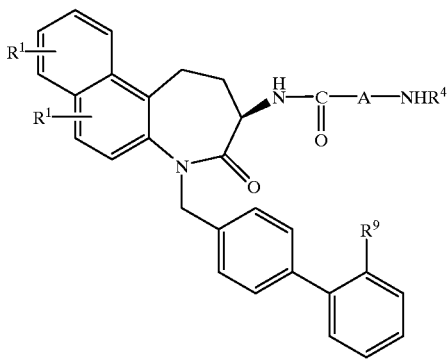

| R¹ R⁹ | A | | R⁴ |
|---|---|---|---|
| H | —CH₂NH—C(=O)—N(CH₃)₂ | —C(CH₃)₂— | H |
| H | —CH₂NH—C(=O)—NHCH(CH₃)₂ | —C(CH₃)₂— | H |
| H | —CH₂N(CH₃)—C(=O)—NHCH₃ | —C(CH₃)₂— | H |
| H | —CH₂NH—C(=O)—NHCH₂Ph | —C(CH₃)₂— | H |
| H | —CH₂NH—C(=O)—N(pyrrolidine) | —C(CH₃)₂— | H |
| H | —CH₂NH—C(=O)—N(morpholine) | —C(CH₃)₂— | H |
| H | —CH₂NH—C(=O)—N(piperazine-NH) | —C(CH₃)₂— | H |

EXAMPLE 8

Utilizing the procedures described in Examples 1 to 6 and general methods of organic synthesis described in the chemical literature and familiar to one skilled in the art, the following compounds of Formula I can be prepared from the appropriately substituted starting materials and reagents.

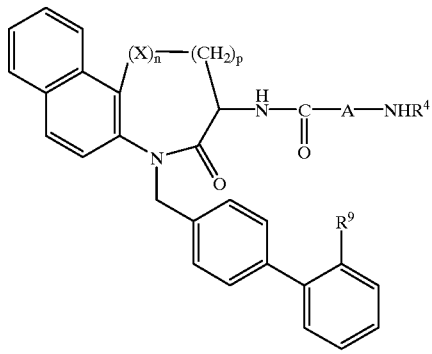

| X | n | p | R⁹ | A | R⁴ |
|---|---|---|---|---|---|
| — | 0 | 3 | —CH₂NH—C(=O)—NHCH₃ | —C(CH₃)₃ | H |
| — | 0 | 3 | —CH₂NH—C(=O)—NHCH₃ | —CH₂—C(CH₃)₂— | —CH₂CH(OH)CH₃ |
| — | 0 | 3 | —CH₂NH—C(=O)—NHCH₃ | —CH₂—C(CH₃)₂— | —CH₂CH(OH)CH₂OH |
| — | 0 | 1 | —CH₂NH—C(=O)—NHCH₃ | —C(CH₃)₃ | H |
| — | 0 | 1 | —CH₂NH—C(=O)—NHCH₃ | —CH₂—C(CH₃)₂— | —CH₂CH(OH)CH₃ |
| — | 0 | 1 | —CH₂NH—C(=O)—NHCH₃ | —CH₂—C(CH₃)₂— | —CH₂CH(OH)CH₂OH |
| — | 0 | 0 | —CH₂NH—C(=O)—NHCH₃ | —C(CH₃)₃ | H |
| — | 0 | 0 | —CH₂NH—C(=O)—NHCH₃ | —CH₂—C(CH₃)₂— | —CH₂CH(OH)CH₃ |
| — | 0 | 0 | —CH₂NH—C(=O)—NHCH₃ | —CH₂—C(CH₃)₂— | —CH₂CH(OH)CH₂OH |
| C=O | 1 | 1 | —CH₂NH—C(=O)—NHCH₃ | —CH₂—C(CH₃)₂— | —CH₂CH(OH)CH₃ |
| CHOH | 1 | 1 | —CH₂NH—C(=O)—NHCH₃ | —CH₂—C(CH₃)₂— | —CH₂CH(OH)CH₃ |
| S | 1 | 0 | —CH₂NH—C(=O)—NHC₂H₅ | —CH₂—C(CH₃)₂— | H |

-continued

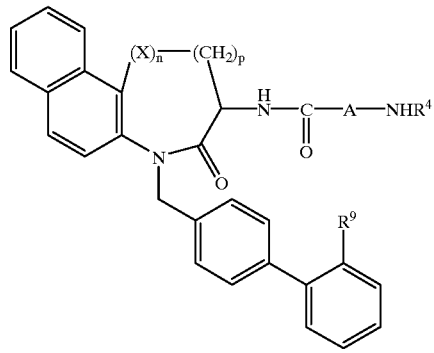

| X | n | p | R⁹ | A | R⁴ |
|---|---|---|---|---|---|
| S | 1 | 0 | —CH₂NH—C(=O)—NHCH₂CH₂OH | —C(CH₃)₂ (stereo) | H |
| S | 1 | 0 | —CH₂NH—C(=O)—NHCH₃ | —CH₂—C(CH₃)₂ (stereo) | —CH(OH)CH₃ (stereo) |
| SO | 1 | 0 | —CH₂NH—C(=O)—NHCH₃ | —CH₂—C(CH₃)₂ (stereo) | H |
| SO | 1 | 0 | —CH₂NH—C(=O)—NHCH₃ | —C(CH₃)₂ (stereo) | H |
| SO | 1 | 0 | —CH₂NH—C(=O)—NHCH₃ | —CH₂—C(CH₃)₂ (stereo) | —CH(OH)CH₃ (stereo) |
| SO | 1 | 0 | —CH₂NH—C(=O)—NHCH₃ | —CH₂—C(CH₃)₂ (stereo) | —CH(OH)CH₂OH (stereo) |
| S | 1 | 2 | —CH₂NH—C(=O)—NH₂ | —CH₂—C(CH₃)₂ (stereo) | H |
| S | 1 | 2 | —CH₂NH—C(=O)—NH₂ | —C(CH₃)₂ (stereo) | H |
| S | 1 | 2 | —CH₂NH—C(=O)—NH₂ | —CH₂—C(CH₃)₂ (stereo) | —CH(OH)CH₃ (stereo) |
| S | 1 | 2 | —CH₂NH—C(=O)—NH₂ | —CH₂—C(CH₃)₂ (stereo) | —CH(OH)CH₂OH (stereo) |
| S | 1 | 2 | —CH₂NH—C(=O)—NH₂ | —CH₂—C(CH₃)₂ (stereo) | H |
| S | 1 | 2 | —CH₂NH—C(=O)—NHCH₂Ph | —C(CH₃)₂ (stereo) | H |
| S | 1 | 2 | —CH₂NH—C(=O)—NHC₂H₅ | —CH₂—C(CH₃)₂ (stereo) | —CH(OH)CH₃ (stereo) |

-continued

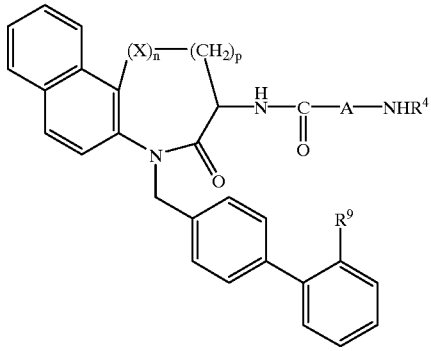

| X | n | p | R⁹ | A | R⁴ |
|---|---|---|---|---|---|
| S | 1 | 2 | —CH$_2$NH—C(=O)—NHPh | —CH$_2$—C(CH$_3$)(CH$_3$) | —CH$_2$CH(OH)CH$_2$OH |
| O | 1 | 1 | —CH$_2$NH—C(=O)—NHCH$_3$ | —CH$_2$—C(CH$_3$)(CH$_3$) | H |
| O | 1 | 1 | —CH$_2$NH—C(=O)—NHCH$_3$ | —C(CH$_3$)(CH$_3$) | H |
| O | 1 | 1 | —CH$_2$NH—C(=O)—NH$_2$ | —CH$_2$—C(CH$_3$)(CH$_3$) | —CH$_2$CH(OH)CH$_3$ |
| O | 1 | 1 | —CH$_2$NH—C(=O)—NHCH$_3$ | —CH$_2$—C(CH$_3$)(CH$_3$) | —CH$_2$CH(OH)CH$_2$OH |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound which is selected from the group consisting of:

2-Amino-2-methyl-N-[3(R)-2,3,4,5-tetrahydro-5-[[2'-[[[(methylamino)carbonyl]amino]methyl][1,1'-biphenyl]-4-yl]methyl]-4-oxo-1H-naphtho[2,1-b]azepin-3(R)-yl]propanamide;

3-Amino-3-methyl-N-[3(R)-2,3,4,5-tetrahydro-5-[[2'-[[[(methylamino)carbonyl]amino]methyl][1,1'-biphenyl]-4-yl]methyl]-4-oxo-1H-naphtho[2,1-b]azepin-3(R)-yl]butanamide;

3-[2(R)-Hydroxypropyl]amino-3-methyl-N-[3(R)-2,3,4,5-tetrahydro-5-[[2'-[[[(methylamino)carbonyl]amino]methyl][1,1'-biphenyl]-4-yl]methyl]-4-oxo-1H-naphtho[2,1-b]azepin-3(R)-yl]butanamide;

3-[2(S),3-Dihydroxypropyl]amino-3-methyl-N-[3(R)-2,3,4,5-tetrahydro-5-[[2'-[[[(methylamino)carbonyl]amino]methyl][1,1'-biphenyl]-4-yl]-methyl]-4-oxo-1H-naphtho[2,1-b]azepin-3(R)-yl]butanamide;

2-Amino-2-methyl-N-[3(R)-2,3,4,5-tetrahydro-5-[[2'-[[[(aminocarbonyl)amino]methyl][1,1'-biphenyl]-4-yl]methyl]-4-oxo-1H-naphtho[2,1-b]azepin-3(R)-yl]propanamide;

3-Amino-3-methyl-N-[3(R)-2,3,4,5-tetrahydro-5-[[2'-[[(aminocarbonyl)amino]methyl][1,1+-biphenyl]-4-yl]methyl]-4-oxo-1H-naphtho[2,1-b]azepin-3(R)-yl]butanamide;

3-[2(R)-Hydroxypropyl]amino-3-methyl-N-[3(R)-2,3,4,5-tetrahydro-5-[[2'-[[((aminocarbonyl)amino]methyl][1,1'-biphenyl]-4-yl]methyl]-4-oxo-1H-naphtho[2,1-b]azepin-3(R)-yl]butanamide;

3-[2(S),3-Dihydroxypropyl]amino-3-methyl-N-[3(R)-2,3,4,5-tetrahydro-5-[[2'-[[(aminocarbonyl)amino]methyl][1,1'-biphenyl]-4-yl]methyl]-4-oxo-1H-naphtho[2,1-b]azepin-3(R)-yl]butanamide;

2-Amino-2-methyl-N-[3(R)-2,3,4,5-tetrahydro-5-[[2'-[[[(ethylamino)carbonyl]amino]methyl][1,1'-biphenyl]-4-yl]methyl]-4-oxo-1H-naphtho[2,1-b]azepin-3(R)-yl]propanamide;

3-Amino-3-methyl-N-[3(R)-2,3,4,5-tetrahydro-5-[[2'-[[[(ethylamino)carbonyl]amino]methyl][1,1'-biphenyl]-4-yl]methyl]-4-oxo-1H-naphtho[2,1-b]azepin-3(R)-yl]butanamide;

3-[2(R)-Hydroxypropyl]amino-3-methyl-N-[3(R)-2,3,4,5-tetrahydro-5-[[2'-[[[(ethylamino)carbonyl]amino]methyl][1,1'-biphenyl]-4-yl]methyl]-4-oxo-1H-naphtho[2,1-b]azepin-3(R)-yl]butanamide;

3-[2(S),3-Dihydroxypropyl]amino-3-methyl-N-[3(R)-2,3,4,5-tetrahydro-5-[[2'-[[[(ethylamino)carbonyl]amino]methyl][1,1'-biphenyl]-4-yl]methyl]-4-oxo-1H-naphtho[2,1-b]azepin-3(R)-yl]butanamide;

2-Amino-2-methyl-N-[3(R -2,3,4,5-tetrahydro-5-[[2'-[[[[(hydroxyethyl)amino]carbonyl]amino]methyl][1,1'-biphenyl]-4-yl]methyl]-4-oxo-1H-naphtho[2,1-b]azepin-3(R)-yl]propanamide;

3-Amino-3-methyl-N-[3(R)-2,3,4,5-tetrahydro-5-[[2'-[[[[(hydroxyethyl)amino]carbonyl]amino]methyl][1,1'-biphenyl]-4-yl]methyl]-4-oxo-1H-naphtho[2,1-b]azepin-3(R)-yl]butanamide;

3-[2(R)-Hydroxypropyl]amino-3-methyl-N-[3(R)-2,3,4,5-tetrahydro-5-[[2'-[[[[(hydroxyethyl)amino]carbonyl]amino]methyl][1,1'-biphenyl]-4-yl]-methyl]-4-oxo-1H-naphtho[2,1-b]azepin-3(R)-yl]butanamide;

3-[2(S),3-Dihydroxypropyl]amino-3-methyl-N-[3(R)-2,3,4,5-tetrahydro-5-[[2'-[[[[(hydroxyethyl)amino]carbonyl]amino]-methyl][1,1'-biphenyl]-4-yl]methyl]-4-oxo-1H-naphtho[2,1-b]azepin-3(R)-yl]butanamide;

2-Amino-2-methyl-N-[3(S)-2,3,4,5-tetrahydro-1-[[2'-[2-[[(methylamino)carbonyl]amino]prop-2-yl][1,1'-biphenyl]-4-yl]methyl]-4-oxo-1H-naphtho[2,1-b]azepin-3(R)-yl]propanamide;

2-Amino-2-methyl-N-[3(R)-2,3,4,5-tetrahydro-5-[[2'-[1-[[(methylamino)carbonyl]amino]ethyl][1,1'-biphenyl]-4-yl]methyl]-4-oxo-1H-naphtho[2,1-b]azepin-3(R)-yl]propanamide;

2-Amino-2-methyl-N-[3(R)-2,3,4,5-tetrahydro-5-[[2'-[[[(methylamino)carbonyl]oxy]methyl][1,1'-biphenyl]-4-yl]methyl]-4-oxo-1H-naphtho[2,1-b]azepin-3(R)-yl]propanamide;

3-Amino-3-methyl-N-[3(R)-2,3,4,5-tetrahydro-5-[[2'-[[[(methylamino)carbonyl]oxy]methyl][1,1'-biphenyl]-4-yl]methyl]-4-oxo-1H-naphtho[2,1-b]azepin-3(R)-yl]butanamide;

3-[2(R)-Hydroxypropyl]amino-3-methyl-N-[3(R)-2,3,4,5-tetrahydro-5-[[2'-[[[(methylamino)carbonyl]oxy]methyl][1,1'-biphenyl]-4-yl]-methyl]-4-oxo-1H-naphtho[2,1-b]azepin-3(R)-yl]butanamide;

3-[2(S),3-Dihydroxypropyl]amino-3-methyl-N-[3(R)-2,3,4,5-tetrahydro-5-[[2'-[[[(methylamino)carbonyl]oxy]methyl][1,1'-biphenyl]-4-yl]methyl]-4-oxo-1H-naphtho[2,1-b]azepin-3(R)-yl]butanamide;

and pharmaceutically acceptable salts thereof.

2. A pharmaceutical composition which comprises an inert carrier and a compound of claim 1.

3. A pharmaceutical composition which comprises a combination of a bisphosphonate compound and a compound of claim 1.

4. The pharmaceutical composition of claim 3 wherein the bisphosphonate compound is alendronate.

5. A method for increasing levels of endogenous growth hormone in a human or an animal which comprises administering to such human or animal an effective amount of a compound of claim 1.

6. A method for increasing feed efficiency, promoting growth, increasing milk production and improving the carcass quality of livestock which comprises administering to such livestock an effective amount of a compound of claim 1.

7. A method for the treatment of a disease or a condition which is benefited by the anabolic effects of enhanced growth hormone levels that comprises administering to a patient in need thereof an effective amount a compound of claim 1.

8. The method of claim 7 wherein the disease or condition is selected from the group consisting of: osteoporosis; catabolic illness; immune deficiency, including that in individuals with a depressed $T_4/T_8$ cell ratio; bone fracture; musculoskeletal impairment in the elderly; growth hormone deficiency in adults or in children; short stature in children; obesity; sleep disorders; cachexia and protein loss due to chronic illness such as AIDS or cancer; and the treatment of patients recovering from major surgery, wounds or burns.

9. A method for the treatment of osteoporosis which comprises administering to a patient with osteoporosis a combination of a bisphosphonate compound and a compound of claim 1.

10. The method of claim 9 wherein the bisphosphonate compound is alendronate.

* * * * *